United States Patent
Yu et al.

(10) Patent No.: US 10,047,341 B2
(45) Date of Patent: Aug. 14, 2018

(54) GENERATION OF KERATINOCYTES FROM PLURIPOTENT STEM CELLS AND MAINTENANCE OF KERATINOCYTE CULTURES

(71) Applicant: FUJIFILM Cellular Dynamics, Inc., Madison, WI (US)

(72) Inventors: Junying Yu, Madison, WI (US); Ying Zhang, Madison, WI (US); Lisa Harms, Madison, WI (US)

(73) Assignee: FUJIFILM Cellular Dynamics, Inc., Madison, WI (US)

( * ) Notice: Subject to any disclaimer, the term of this patent is extended or adjusted under 35 U.S.C. 154(b) by 0 days.

(21) Appl. No.: 14/881,747

(22) Filed: Oct. 13, 2015

(65) Prior Publication Data

US 2016/0102289 A1 Apr. 14, 2016

Related U.S. Application Data

(60) Provisional application No. 62/063,720, filed on Oct. 14, 2014.

(51) Int. Cl.

| | |
|---|---|
| *C12N 5/00* | (2006.01) |
| *C12N 5/02* | (2006.01) |
| *C12N 5/071* | (2010.01) |
| *G01N 33/50* | (2006.01) |
| *A61K 35/36* | (2015.01) |

(52) U.S. Cl.
CPC ............ *C12N 5/063* (2013.01); *A61K 35/36* (2013.01); *G01N 33/5073* (2013.01); *C12N 2500/38* (2013.01); *C12N 2500/90* (2013.01); *C12N 2501/01* (2013.01); *C12N 2501/10* (2013.01); *C12N 2501/11* (2013.01); *C12N 2501/113* (2013.01); *C12N 2501/15* (2013.01); *C12N 2501/155* (2013.01); *C12N 2501/165* (2013.01); *C12N 2501/33* (2013.01); *C12N 2501/385* (2013.01); *C12N 2501/998* (2013.01); *C12N 2501/999* (2013.01); *C12N 2506/02* (2013.01); *C12N 2506/45* (2013.01); *C12N 2533/52* (2013.01)

(58) Field of Classification Search
CPC ............... C12N 5/063; C12N 2501/01; C12N 2501/10; C12N 2506/02; C12N 2506/45; G01N 33/5073

USPC ................................ 435/366, 377, 405, 406
See application file for complete search history.

(56) References Cited

U.S. PATENT DOCUMENTS

| | | |
|---|---|---|
| 2012/0142103 A1 | 6/2012 | Nishida et al. |
| 2013/0236904 A1 | 9/2013 | Choi et al. |

OTHER PUBLICATIONS

Narsinh et al., 2011, Molecular Therapy, vol. 9, No. 4, p. 635-638.*
Bellin et al., 2012, Nature reviews/Molecular Cell Biology, vol. 13, p. 713-726.*
Burridge et al., 2011, PLoS ONE, vol. 6, No. 4, e18293, p. 1-16.*
Wang, Yigang, 2014, New Journal of Science, vol. 2014, Article ID 756240, pp. 1-22.*
Cerqueira et al., "Cell sheet technology-driven re-epithelialization and neovascularization of skin wounds," *Acta Biomaterialia*, 10(7):3145-3155, 2014.
Kawasaki et al., "Induction of midbrain dopaminergic neurons from ES cells by stromal cell-derived inducing activity," *Neuron*, 28:31-40, 2000.
Kogut et al., "Differentiation of human induced pluripotent stem cells into a keratinocyte lineage," *Methods in Molecular Biology*, 1195:1-12, 2014.
Lian et al., "A Small Molecule Inhibitor of Src Family Kinases Promotes Simple Epithelial Differentiation of Human Pluripotent Stem Cells," PLoS ONE, 8:e60016, 2013.
Metallo et al., "Human embryonic stem cell-derived keratinocytes exhibit an epidermal transcription program and undergo epithelial morphogenesis in engineered tissue constructs," *Tissue Engineering Part A*, 16(1): 213-223, 2010.
Metallo et al., "Retinoic acid and bone morphogenetic protein signaling synergize to efficiently direct epithelial differentiation of human embryonic stem cells," *Stem Cells*, 26(2):372-380, 2008.
PCT International Search Report and Written Opinion issued in International Application No. PCT/US2015/055284, dated Mar. 31, 2016.
PCT Invitation to Pay Additional Fees issued in International Application No. PCT/US2015/055284, dated Jan. 20, 2016.
Rheinwald, "The quest to derive keratinocytes from pluripotent stem cells," *Current Pathobiology Reports*, 1(2):119-128, 2013.

* cited by examiner

*Primary Examiner* — Shin Lin Chen
(74) *Attorney, Agent, or Firm* — Parker Highlander PLLC

(57) ABSTRACT

Provided herein are methods for the generation of functional keratinocyte stem cells that are differentiated directly from human ESCs/iPSCs in a chemically defined serum-free cell culture system, as well as cells derived therefrom and methods of use thereof. Also provided are methods for culturing primary keratinocytes.

31 Claims, 22 Drawing Sheets

A

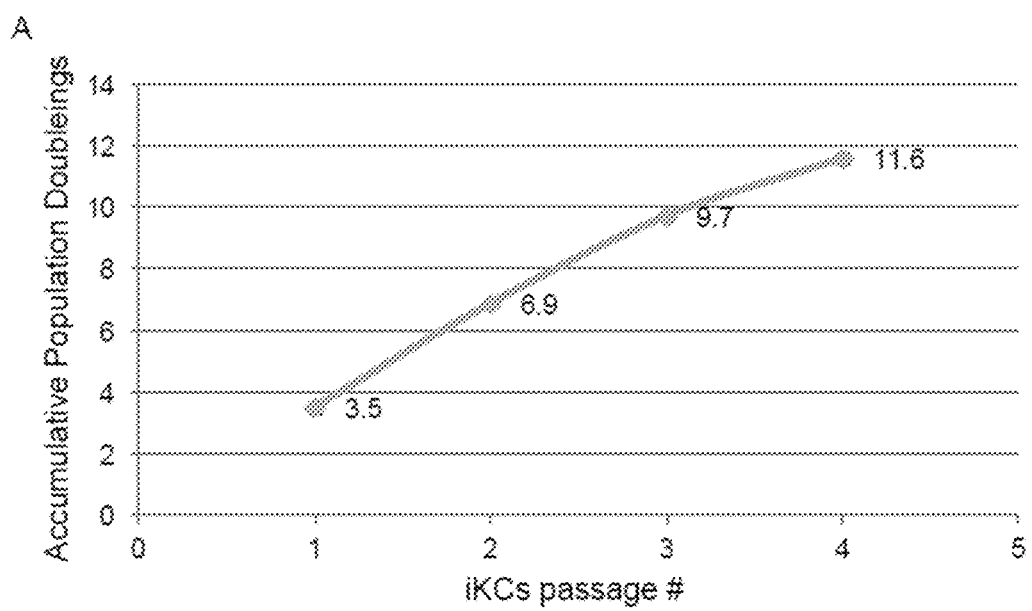
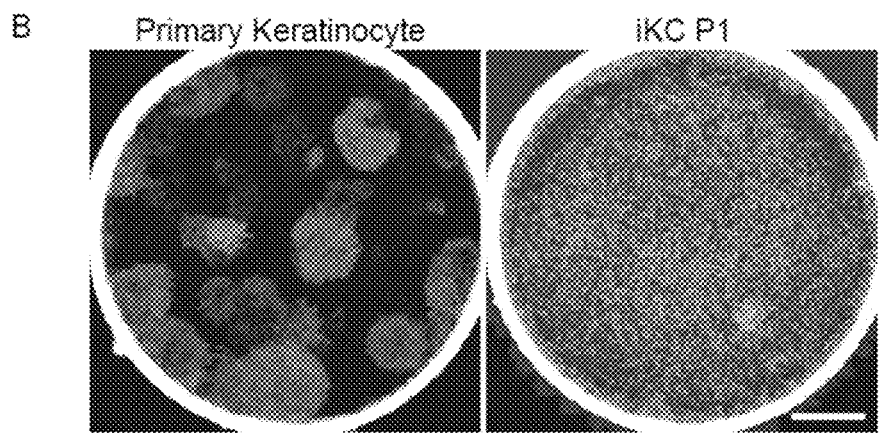
FIGs. 5A-B

A
Primary KCs on DED
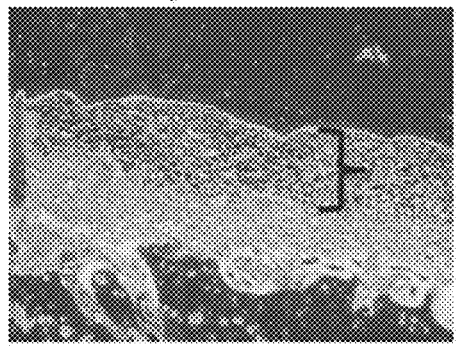
P1 iKCs on DED
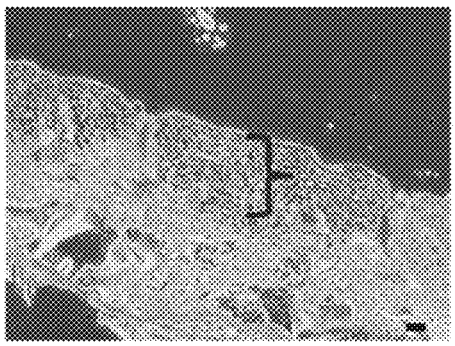
B
mKCs + mFBs
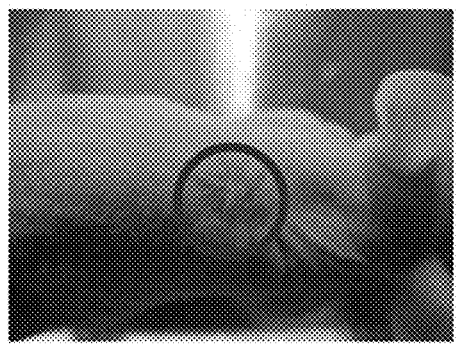
hKCs + hFBs
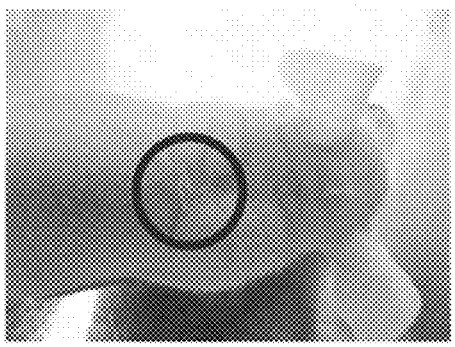
iKCs + hFBs, rep 1
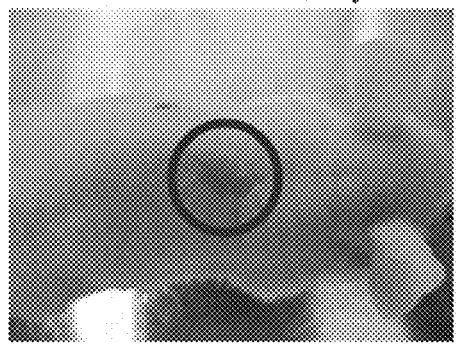
iKCs + hFBs, rep 2
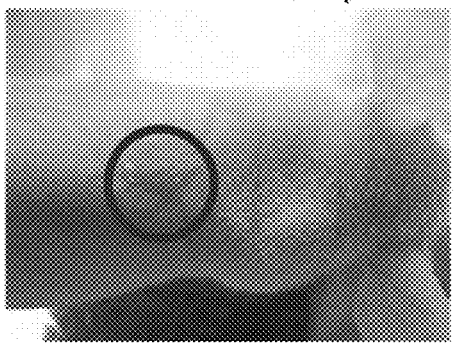
FIGs. 6A-B

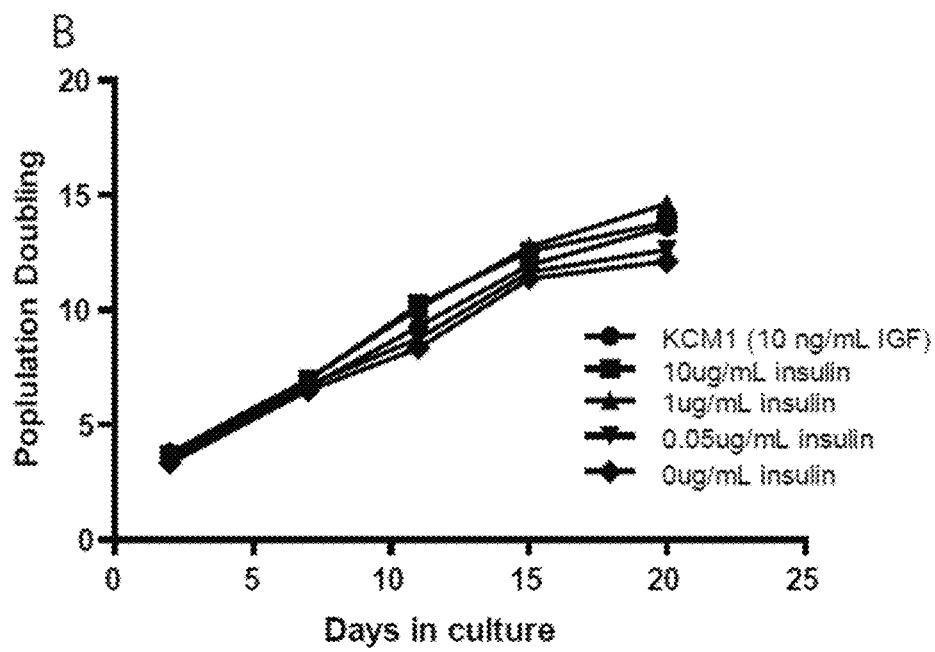
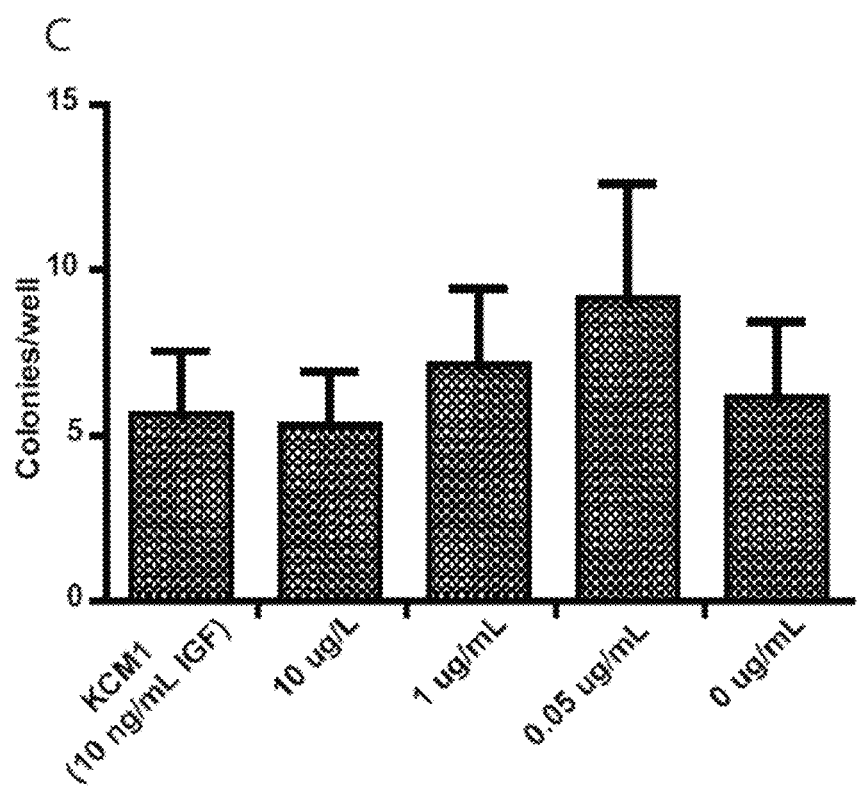
FIGs. 7B-C

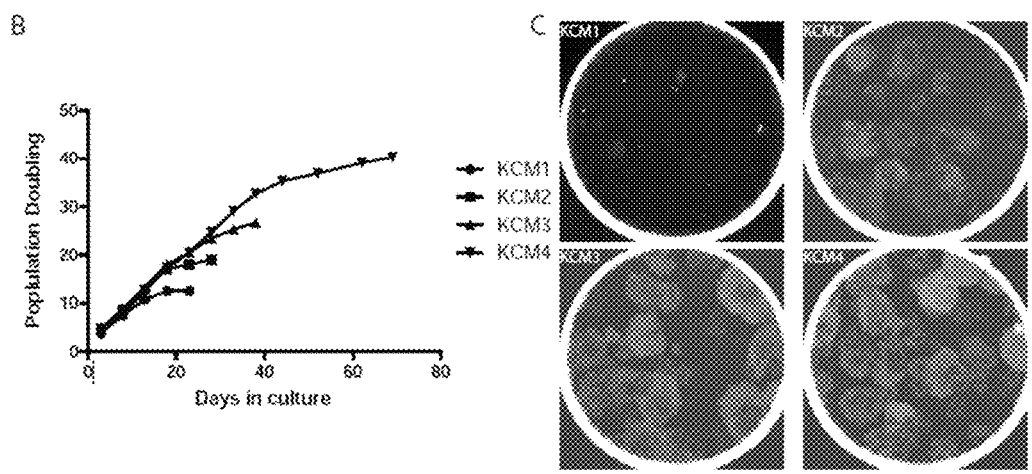
FIGs. 8B-C

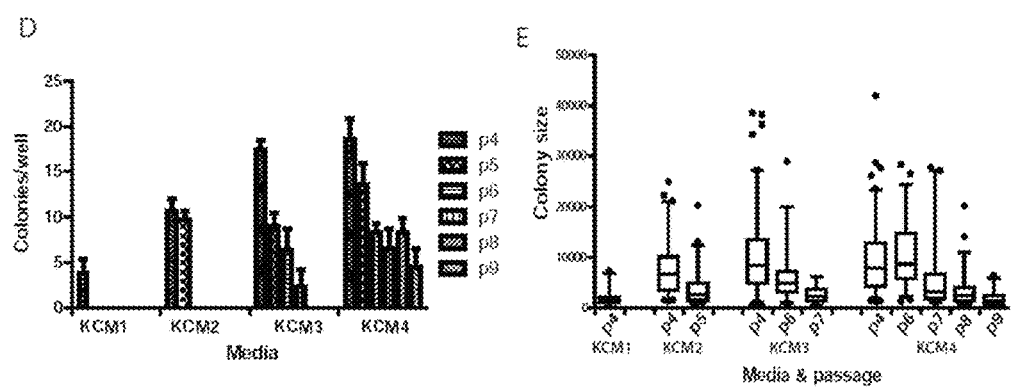
FIGs. 8D-E

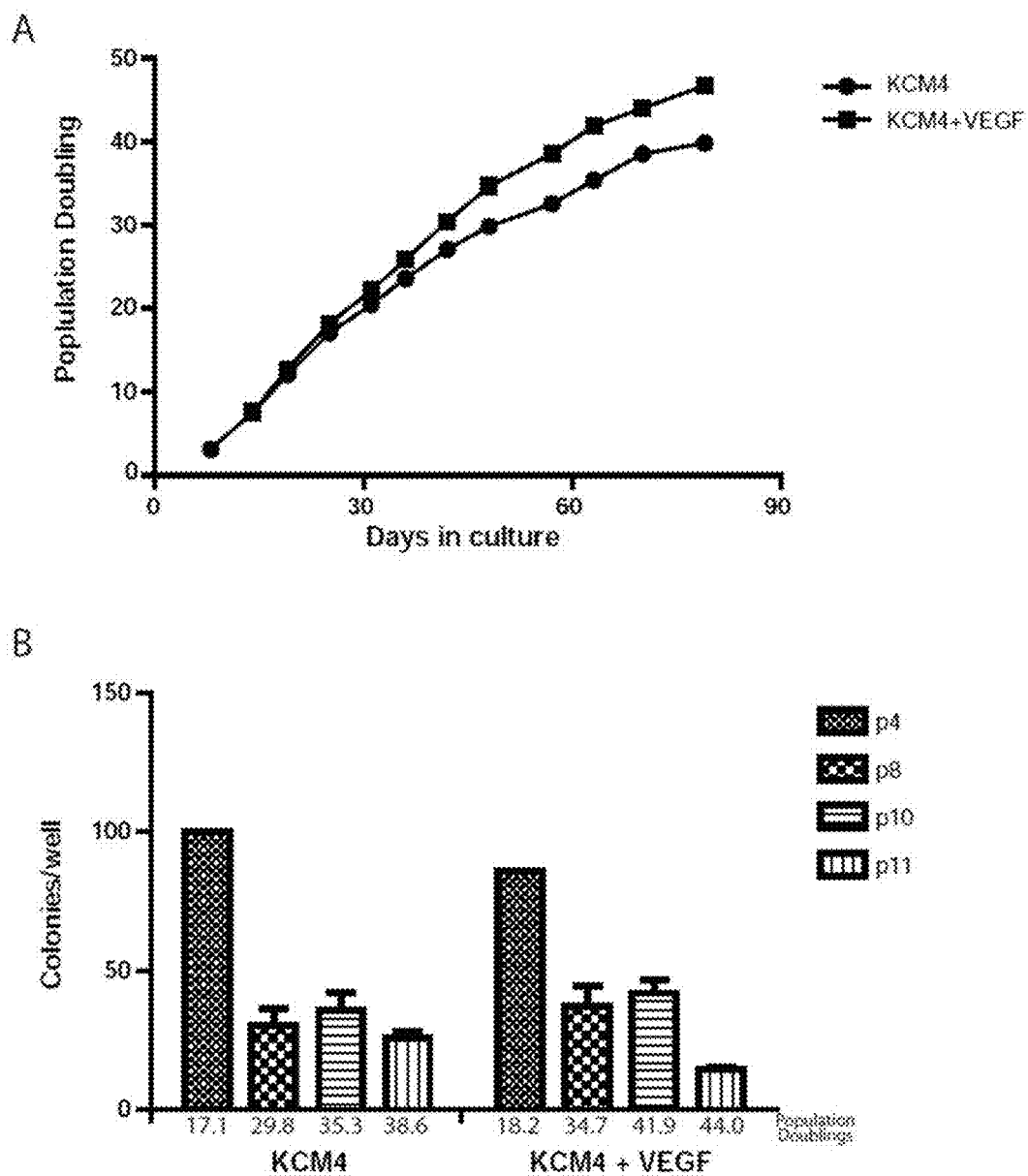
FIGs. 9A-B

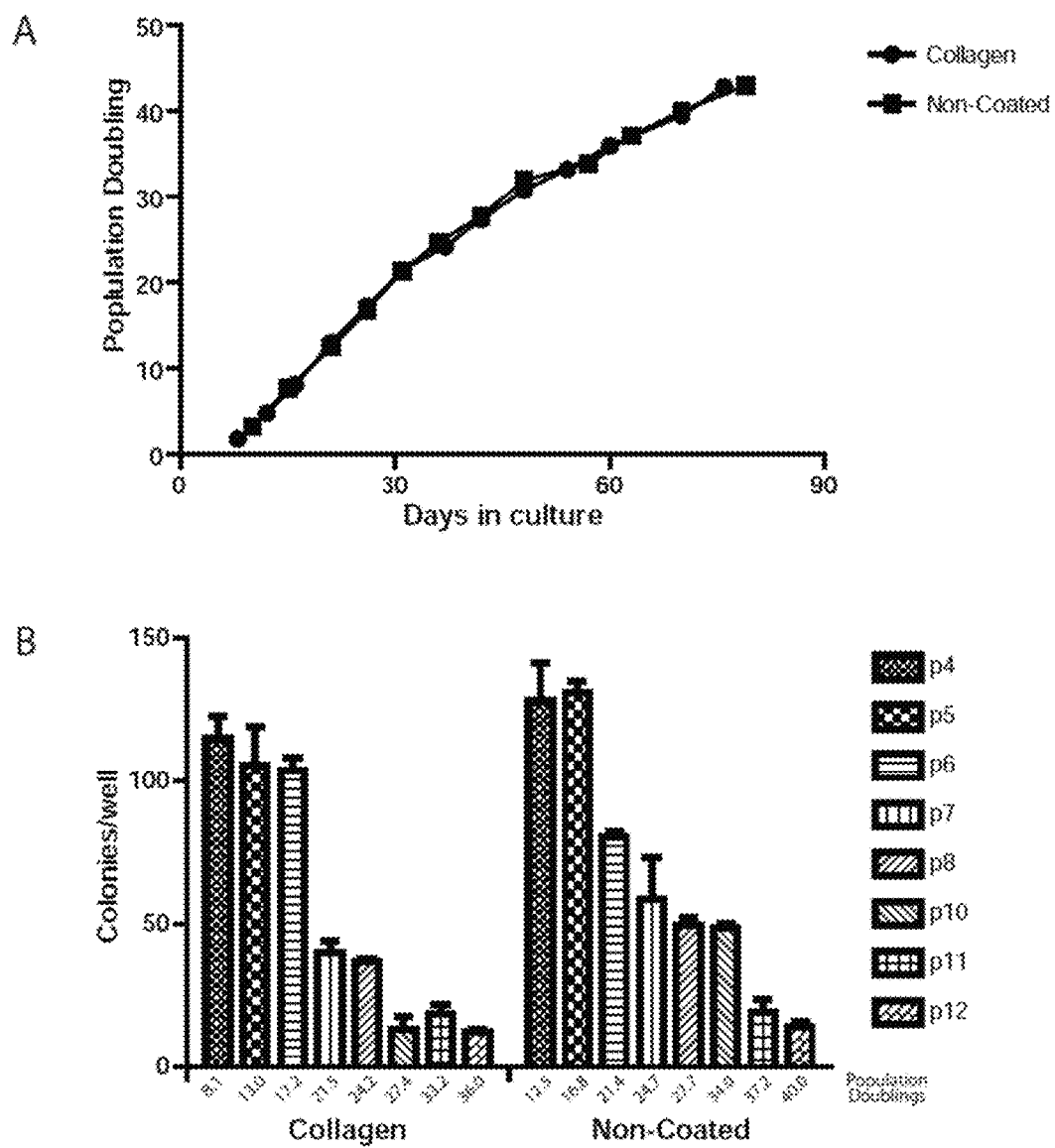
FIGs. 10A-B

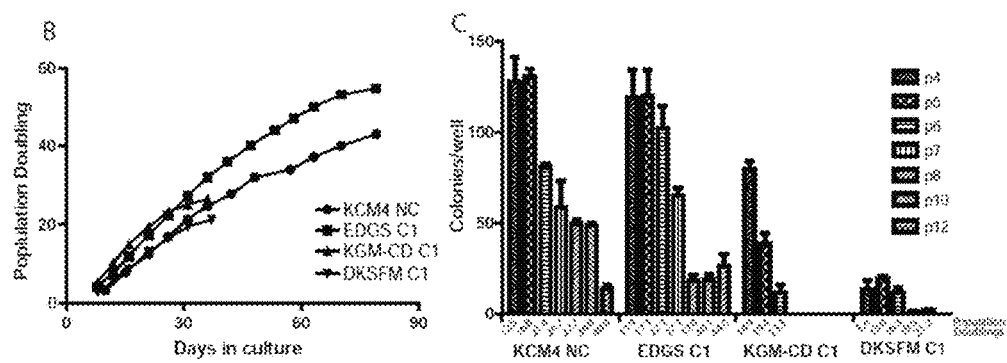
FIGs. 12B-C

GENERATION OF KERATINOCYTES FROM PLURIPOTENT STEM CELLS AND MAINTENANCE OF KERATINOCYTE CULTURES

This application claims priority to U.S. Application No. 62/063,720 filed on Oct. 14, 2014, the entire disclosure of which is specifically incorporated herein by reference in its entirety without disclaimer.

BACKGROUND OF THE INVENTION

1. Field of the Invention

The present invention relates generally to the fields of stem cells and differentiated cells. More particularly, it concerns the generation of induced keratinocyte stem cells (iKCs) from undifferentiated cells and methods of culturing primary keratinocytes.

2. Description of Related Art

Human embryonic stem cells (ESCs) and induced pluripotent stem cells (iPSC) are capable of long-term proliferation in vitro, while retaining the potential to differentiate into all cell types of the body, including keratinocytes. Thus, these pluripotent cells have the potential to provide an unlimited supply of patient-specific functional keratinocytes for both transplantation therapies and cosmetics/drug development.

To date, several groups have reported procedures to differentiate mouse and human ES/iPS cells to epidermal keratinocytes (cytokeratin 14-positive). Metallo et al. (2010) used retinoic acid and BMP4 on embryoid bodies and mono-layer culture on collagen IV-coated surface without feeder cells to induce keratinocyte differentiation from human ES cells. Kawasaki et al. (2000) reported a method using feeder cells promote neural differentiation of mouse ES cells, and that BMP4 addition promotes the initiation of epidermal determination from neuronal ectoderm. Lian et al. (2013) described a method using small molecule inhibitor of Src family kinases to derive simple epithelial progenitors, which further differentiate to epidermal keratinocytes in serum-free conditions. However, none of these methods have generated epidermal keratinocyte stem cells (cytokeratin 14 and cytokeratin 15 double positive) with a proliferative capacity of more than two population doublings or long-term engraftability.

SUMMARY OF THE INVENTION

In one embodiment, a method is provided for generating engraftable keratinocyte stem cells by differentiation of pluripotent stem cells comprising: (a) forming aggregates of the pluripotent stem cells in a suspension culture in the presence of a defined basal medium; (b) culturing the aggregates in a suspension culture in the presence of an initiation culture medium comprising retinoic acid and BMP4 to effect the formation of initiated aggregates; (c) culturing the initiated aggregates in a keratinocyte progenitor culture medium comprising cholera toxin and a TGFβR1 kinase inhibitor to effect the formation of a cell population comprising keratinocyte progenitors; and (d) culturing the keratinocyte progenitors in a keratinocyte stem cell maturation medium to effect the formation of a cell population comprising engraftable keratinocyte stem cells.

In various aspects, the method may further comprise maintaining the keratinocyte stem cells in culture in a keratinocyte stem cell maintenance medium. In certain aspects, the keratinocyte stem cells may be maintained for 1, 2, 3, 4, 5, 6, 7, 8, 9, 10, 11, 12, 13, 14, 15, 16, 17, 18, 19, 20, or any range derivable therein. Preferably, the cells may be maintained for at least five or at least ten population doublings. In certain aspects, the keratinocyte stem cells may be at least 1%, 5%, 10%, 15%, 20%, 25%, 30%, 40%, 45%, 50%, 60%, 70%, 80%, 90%, 95%, 98%, 99%, or 100% pure. Preferably the keratinocyte stem cells may be at least 90% or 95% pure.

In certain aspects, the pluripotent stem cells may be induced pluripotent stem (iPS) cells or embryonic stem cells. The stem cells may also include multipotent stem cells, oligopotent stem cells, or unipotent stem cells. The stem cells may also include fetal stem cells or adult stem cells, such as epithelial stem cells, and skin stem cells. In certain aspects, the stem cells may be isolated from umbilical, placenta, amniotic fluid, chorion villi, blastocysts, bone marrow, adipose tissue, brain, peripheral blood, cord blood, menstrual blood, blood vessels, skeletal muscle, skin, and liver.

In some aspects, the pluripotent stem cells may be cultured in a serum-free medium prior to step (a). In some aspects, the pluripotent stem cells may be cultured on a non-cellular matrix component prior to step (a).

In various aspects, forming aggregates may comprise dissociating the pluripotent stem cells into an essentially single cell culture. In certain aspects, the essentially single cell culture for the present method may comprise at least or about $10^4$, $10^5$, $10^6$, $10^7$, $10^8$, $10^9$, $10^{10}$, $10^{11}$, $10^{12}$, $10^{13}$ cells or any range derivable therein. The essentially single cell culture may comprise an initial seeding density of at least or about 10, $10^1$, $10^2$, $10^3$, $10^4$, $10^5$, $10^6$, $10^7$, $10^8$ cells/mL, or any range derivable therein. In certain aspects, the culture medium in step (a) may be a chemically-defined culture medium, such as, for example, TeSR medium. In some aspects, the culturing in step (a) may be performed for a time period of about one, two, or three days. Preferably, said culturing is performed for a time period of about one day. In various aspects, the culturing in step (a) may be performed in the presence of a myosin light chain kinase inhibitor.

In some aspects, the culturing in step (b) may be performed for a time period of at least or about 1, 2, 3, 4, 5, 6, 7, 8, 9, 10, 11, 12, 13, 14, 15, 16, 17, 18, 19, 20 days, or any range derivable therein. Preferably, said culturing is performed for a time period from about one day to about five days, such as, for example, for a time period of about three days. In certain aspects, the suspension culture in step (a) and/or (b) may be maintained as a static suspension culture. In certain aspects, the suspension culture in step (a) and/or (b) may be maintained as a dynamic suspension culture.

In certain aspects, the culturing in step (c) may be performed for a time period of at least or about 1, 2, 3, 4, 5, 6, 7, 8, 9, 10, 11, 12, 13, 14, 15, 16, 17, 18, 19, 20 days, or any range derivable therein. Preferably, said culturing is performed for a time period from about eight to about 14 days, such as, for example, for a time period of about ten days. In some aspects, the culturing in step (c) may be performed as an adherent culture. In some aspects, the culturing in step (c) may be performed on an extracellular matrix component. In some aspects, the culturing in step (c) may be performed on a non-cellular matrix component.

In various aspects, the keratinocyte progenitor culture medium may further comprise EGF, FGF1, a cyclic AMP analog, niacinamide, ascorbic acid, or a combination thereof. In some aspects, the keratinocyte progenitor culture medium may further comprise EGF and niacinamide. In certain aspects, the calcium level in the keratinocyte progenitor culture medium may not be greater than about 0.2 mM and preferably not greater than about 0.12 mM.

In certain aspects, the keratinocyte progenitors may express cytokeratin 14 and/or p63. Said expression may be detected by protein expression analysis, for example ELISA or FACS analysis, or RNA expression analysis, for example qRT-PCR.

In certain aspects, the culturing in step (d) may be performed for a time period of at least or about 1, 2, 3, 4, 5, 6, 7, 8, 9, 10, 11, 12, 13, 14, 15, 16, 17, 18, 19, 20 days, or any range derivable therein. Preferably, said culturing is performed for a time period from about four days to about eight days, such as, for example, for a time period of about six days. In some aspects, the culturing in step (d) may be performed as an adherent culture. In some aspects, the culturing in step (d) may be performed on an extracellular matrix component. In some aspects, the culturing in step (d) may be performed on a non-cellular matrix component.

In various aspects, the keratinocyte stem cell maturation medium may comprise cholera toxin, a TGFβR1 kinase inhibitor, EGF, FGF1, a cyclic AMP analog, niacinamide, or a combination thereof.

In certain aspects, the keratinocyte stem cells may express cytokeratin 15 and/or CD49f. Said expression may be detected by protein expression analysis, for example ELISA or FACS analysis, or RNA expression analysis, for example qRT-PCR.

In one embodiment, a method is provided for assessing a compound for a pharmacological or toxicological effect on a keratinocyte, comprising: (a) contacting a keratinocyte provided by a method of the present embodiments with the compound; and (b) assaying a pharmacological or toxicological effect of the compound on the keratinocyte.

In one embodiment, a transplantable sheet of epithelial cells is provided comprising keratinocyte stem cells generated according to a method of the present embodiments. In some aspects, the sheet may be further defined as a transplantable sheet of skin epithelial cells. In some aspects, the sheet may be further defined as a transplantable sheet of corneal epithelial cells.

In one embodiment, a method is provided for treating a patient in need thereof, comprising transplanting a transplantable sheet of epithelial cells of the present embodiments to the patient. In certain aspects, the keratinocyte stem cells may be autologous to the patient.

In one embodiment, a defined keratinocyte culture medium is provided comprising niacinamide and BMP4. In certain aspects, the medium may be further defined as comprising about 3 mM niacinamide. In certain aspects, the medium may be further defined as comprising about 0.5 ng/mL BMP4. In some aspects, the medium may further comprise VEGF and/or insulin. In some aspects, the medium may further comprise calcium, ethanolamine and phosphorylethanolamine, transferrin, hydrocortisone, FGF1, EGF, IGF1, T3, L-carnitine, a cyclinc AMP analogue, and/or cholera toxin. In some aspects, the method may be further defined as comprising 80 µM calcium, 0.1 mM ethanolamine, 0.1 mM phosphorylethanolamine, 5 µg/mL transferrin, 0.2 µg/mL hydrocortisone, 1 ng/mL FGF1, 0.5 ng/mL EGF, 10 ng/mL IGF1, 10 nM T3, 5 µM L-carnitine, 0.2 mM 8-Br-cAMP, 100 µM cholera toxin, 3 mM niacinamide, 0.5 ng/mL BMP4, 25 ng/mL VEGF, and 10 µg/mL insulin.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 5A-B. Growth potential and stemness of iKCs. (A) Proliferative potential of iKCs in maintenance conditions. iKCs were passaged with 0.1% Trypsin in Versene onto gelatin coated Nunclon 6-well plates at 50,000 cells per well. Cells were fed with maintenance medium every other day and passaged again on the fifth day of each plating. Total cell numbers were recorded at each passage to calculate population doubling numbers. (B) Colony Formation Assay (CFA) images of iKCs and primary keratinocytes. Cells were plated at 250 cells per well on a 6-well plate, and allowed to grow for two weeks. For primary keratinocytes, blank non-cell culture treated plates were used for optimal growth; while for iKCs plates that were previously cultured with primary keratinocytes were used to have the natural Laminin deposits as the basement membrane. At the end of culture, cells were fixed with 2% formaldehyde and stained with Hoechst. The whole plates were imaged with the Molecular Devices ImageXpress high content imager. Scale bar, 1 cm.

FIGS. 6A-B. Differentiation potential of iKCs. (A) Differentiation and stratification of iKCs on mouse deepidermized dermis (DED). After two weeks of culture in transwells, DED-grafts were lifted and embedded in OCT compound for cryosectioning. Sections (16 µM) were cut and stained with Haematoxylin. Grafted cells show pink staining for their nucleus. Brackets point to the multiple layer of live cells on top of the white DED tissue underneath. (B) Engraftability of iKCs on the back of FoxN1 immunodeficient nude mice. The pictures taken at three weeks post surgery showed that iKCs (2 replicates, or reps), when grafted together with human neonatal foreskin fibroblasts (hFBs), were able to cover and heal the initial wound on the skin to a similar extent as primary mouse and human keratinocytes (mKCs and hKCs). Mice grafted with hFBs alone died between week 1 and 2 post-surgery. Note the lack of residual hair on the iKC grafts. Scale bar, 500 µM.

FIGS. 7A-D. Insulin and IGF both support human neonatal foreskin primary keratinocyte growth. (A) Bright-field images of primary keratinocytes cultured in KCM1 with either IGF or various concentrations of insulin (0-10 µg/mL). Scale bar 200 µm. (B) Long-term culture of primary keratinocytes in KCM1. (C & D) CFAs of keratinocytes cultured in KCM1 variations. Data from passage 6 are shown.

FIGS. 8A-E. Niacinamide and BMP-4 extend the life span of primary keratinocytes in culture. (A) Bright-field images of primary keratinocytes cultured in different medium formulations (p3). Scale bars 200 µm. (B) Long-term culture of primary keratinocytes in different medium formulations. (C) CFAs with keratinocytes (p4) cultured in different medium formulations. (D & E) Quantification of CFAs with keratinocytes cultured in KCM1, KCM2, KCM3 and KCM4.

FIGS. 9A-C. VEGF increased the proliferative potential of primary keratinocytes. (A) Long-term culture of cells grown in KCM4 and KCM4+VEGF (25 ng/mL). (B & C) Positive effect of VEGF in the CFA in later passages.

FIGS. 10A-C. Keratinocytes can be cultured on either collagen 1 or non-coated plastic plates. (A) Long-term culture of cells grown in KCM4 on either collagen 1 coated or non-coated plates. (B & C) Cells grown on the non-coated plates performed slightly better in the CFA than those grown on collagen.

FIGS. 12A-D. KCM4 performs similarly to commercially available chemically defined media. KCM4 was compared to three different chemically defined media: Invitrogen's Defined Keratinocyte Serum Free Medium (DKSFM), EpiLife Defined Growth Supplement (EDGS), and Lonza's Keratinocyte Growth Medium-Chemically Defined (KGM-CD). Cells cultured in the commercial media were grown on collagen I (C1)-coated plates, as recommended by the manufacturer. Non-coated (NC)-plates were used for KCM4 culture. (A) Bright-field images of primary KCs cultured in different media (P3 DSKFM, EDGS and KGM-CD and P5 KCM4). Scale bars 200 µm. (B) Long-term culture of primary keratinocytes in different media. (C & D) CFAs of keratinocytes cultured in different media. KCM4 performs better than the other media with regard to colony number and size.

DESCRIPTION OF ILLUSTRATIVE EMBODIMENTS

Primary human keratinocytes are used to generate epithelial sheets to apply to damaged skin epithelium and corneal epithelium. Both infant foreskin keratinocytes and autologous keratinocytes have been harvested and expanded in vitro to produce these epithelial sheets. However, the quantity and quality of donor cells often impose limitations on primary keratinocyte transplantations, in addition to adverse immune responses. Furthermore, human keratinocyte-derived epithelial sheets are in demand for cosmetic testing and drug development. The responses of donor-derived keratinocytes to individual compounds provide invaluable insights to how a donor would react under both physiological and pathological conditions, thus opening the gate to personalized cosmetics and skin treatments.

Figure 1:
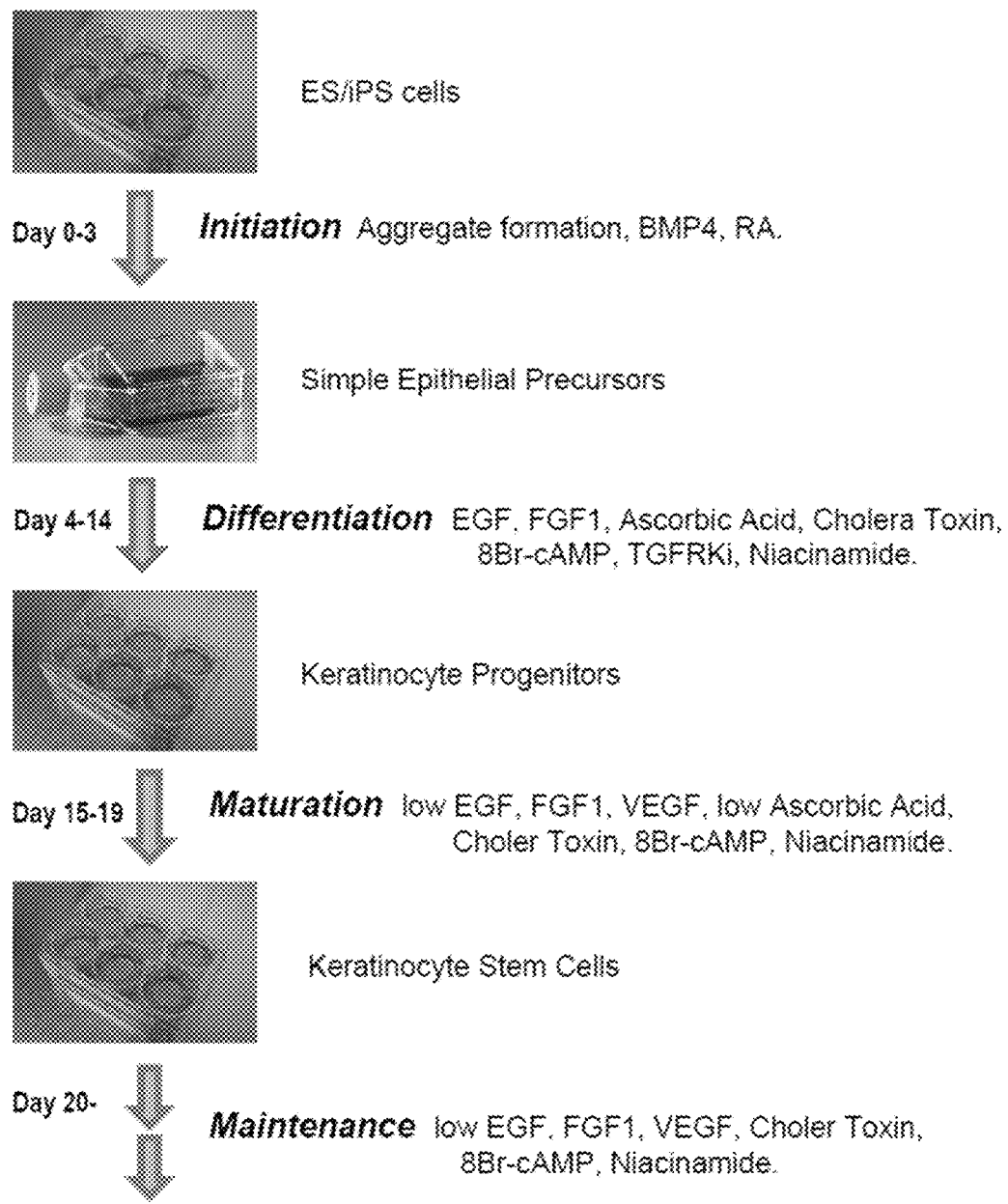
FIG. 1. Normal differentiation of induced keratinocyte stem cells (iKCs) from human ESC/iPSCs. Keratinocyte stem cells can be generated from ESC/iPSCs in four steps: Initiation, Differentiation, Maturation, and Maintenance. Complete formulations of chemically defined culture medium (FBS- and BSA-free) at each step are illustrated in Tables 1-4.

Provided herein are methods to provide functional keratinocyte stem cells that are differentiated directly from human ESCs/iPSCs in a chemically defined serum-free cell culture system, as well as cell derived therefrom. The differentiation and growth stimuli are administered to the cells along four stages, including initiation, differentiation, maturation, and maintenance (FIG. 1). With this method, induced keratinocyte stem cells (iKCs) are able to be generated efficiently with the enhanced proliferative potential of >10 population doublings. These iKCs express epidermal keratinocyte stem cell markers cytokeratin 14, cytokeratin 15, and CD49f. In addition, when mixed with human skin fibroblasts, iKCs are engraftable to the back of immunodeficient nude mice to heal a full thickness epidermal removal wound.

II. Definitions

As used herein in the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

The term "cultured," as used herein, in reference to cells can refer to one or more cells that are undergoing cell division or not undergoing cell division in an in vitro environment. An in vitro environment can be any medium known in the art that is suitable for maintaining cells in vitro, such as suitable liquid media or agar, for example. Specific examples of suitable in vitro environments for cell cultures are described in Culture of Animal Cells: a manual of basic techniques (1994); Cells: a laboratory manual (1998); and Animal Cells: culture and media (1994).

The term "cell line" as used herein can refer to cultured cells that can be passaged at least one time without terminating. The invention relates to cell lines that can be passaged indefinitely. Cell passaging is defined hereafter.

The term "suspension" as used herein can refer to cell culture conditions in which cells are not attached to a solid support. Cells proliferating in suspension can be stirred while proliferating using an apparatus well known to those skilled in the art.

The term "monolayer" as used herein can refer to cells that are attached to a solid support while proliferating in suitable culture conditions. A small portion of cells proliferating in a monolayer under suitable growth conditions may be attached to cells in the monolayer but not to the solid support.

The term "plated" or "plating" as used herein in reference to cells can refer to establishing cell cultures in vitro. For example, cells can be diluted in cell culture media and then added to a cell culture plate, dish, or flask. Cell culture plates are commonly known to a person of ordinary skill in the art. Cells may be plated at a variety of concentrations and/or cell densities.

The term "cell plating" can also extend to the term "cell passaging." Cells of the invention can be passaged using cell culture techniques well known to those skilled in the art. The term "cell passaging" can refer to a technique that involves the steps of (1) releasing cells from a solid support or substrate and disassociation of these cells, and (2) diluting the cells in media suitable for further cell proliferation. Cell passaging may also refer to removing a portion of liquid medium containing cultured cells and adding liquid medium to the original culture vessel to dilute the cells and allow further cell proliferation. In addition, cells may also be added to a new culture vessel that has been supplemented with medium suitable for further cell proliferation.

The term "hypoxia" and "hypoxic conditions" as used herein can refer to conditions characterized by a lower oxygen concentration as compared to the oxygen concentration of ambient air (approximately 15%-20% oxygen). In one aspect, hypoxic conditions are characterized by an oxygen concentration less than about 10%. In another aspect hypoxic conditions are characterized by an oxygen concentration of about 1% to 10%, 1% to 9%, 1% to 8%, 1% to 7%, 1% to 6%, 1% to 5%, 1% to 4%, 1% to 3%, or 1% to 2%, or any range derivable therein.

The term "proliferation" as used herein in reference to cells can refer to a group of cells that can increase in number over a period of time.

The term "permanent" or "immortalized" as used herein in reference to cells can refer to cells that may undergo cell division and double in cell numbers while cultured in an in vitro environment a multiple number of times until the cells terminate. A permanent cell line may double over 10 times before a significant number of cells terminate in culture. Preferably, a permanent cell line may double over 20 times or over 30 times before a significant number of cells terminate in culture. More preferably, a permanent cell line may double over 40 times or 50 times before a significant number of cells terminate in culture. Most preferably, a permanent cell line may double over 60 times before a significant number of cells die in culture.

"Differentiation" is a process by which a less specialized cell becomes a more specialized cell to form progeny of at least one new cell type, either in culture or in vivo, than it would have under the same conditions without differentiation. "Dedifferentiation" is a cellular process in which a partially or terminally differentiated cell reverts to an earlier developmental stage, such as pluripotency or multipotency. "Transdifferentiation" is a process of transforming one differentiated cell type into another differentiated cell type. Under certain conditions, the proportion of progeny with characteristics of the new cell type may be at least about 1%, 5%, 25% or more in order of increasing preference.

"Multipotent" implies that a cell is capable, through its progeny, of giving rise to several different cell types found in an adult animal.

"Pluripotent" implies that a cell is capable, through its progeny, of giving rise to all the cell types that comprise the adult animal, including the germ cells. Embryonic stem cells, induced pluripotent stem cells, and embryonic germ cells are pluripotent cells under this definition.

The term "autologous cells" as used herein refers to donor cells that are genetically identical with the recipient.

The term "totipotent" as used herein can refer to a cell that gives rise to a live born animal. The term "totipotent" can also refer to a cell that gives rise to all of the cells in a particular animal. A totipotent cell can give rise to all of the cells of an animal when it is utilized in a procedure for developing an embryo from one or more nuclear transfer steps.

Totipotent cells may also be used to generate incomplete animals, such as those useful for organ harvesting, e.g., having genetic modifications to eliminate growth of an organ or appendage by manipulation of a homeotic gene. Additionally, genetic modification rendering oocytes, such as those derived from ES cells, incapable of development in utero would ensure that human-derived ES cells could not be used to derive human oocytes for reproduction and only for applications such as therapeutic cloning.

The term "embryonic stem cell" as used herein can refer to pluripotent cells isolated from an embryo that are maintained in in vitro cell culture. Such cells are rapidly dividing cultured cells isolated from cultured embryos that retain in culture the ability to give rise, in vivo, to all the cell types that comprise the adult animal, including the germ cells. Embryonic stem cells may be cultured with or without feeder cells. Embryonic stem cells can be established from embryonic cells isolated from embryos at any stage of development, including blastocyst stage embryos and pre-blastocyst stage embryos. Embryonic stem cells may have a rounded cell morphology and may grow in rounded cell clumps on feeder layers. Embryonic stem cells are well known to a person of ordinary skill in the art. See, e.g., WO 97/37009; Yang & Anderson (1992); Piedrahita et al. (1998); Wianny et al. (1997); Moore & Piedrahita (1997); Moore & Piedrahita (1996); Wheeler (1994); Hochereau-de Reviers & Perreau (1993); Strojek et al. (1990); Piedrahita et al. (1990); and Evans et al. (1990).

The term "reprogramming" or "reprogrammed" as used herein may refer to materials and methods that can convert a more specialized cell into a pluripotent cell.

The term "isolated" as used herein can refer to a cell that is mechanically separated from another group of cells. Examples of a group of cells are a developing cell mass, a cell culture, a cell line, and an animal.

The term "differentiated cell" as used herein can refer to a precursor cell that has developed from an unspecialized phenotype to a specialized phenotype. For example, embryonic cells can differentiate into an epithelial cell lining of the intestine. Differentiated cells can be isolated from a fetus or a live born animal, for example.

The term "undifferentiated cell" as used herein can refer to a precursor cell that has an unspecialized phenotype and is capable of differentiating. An example of an undifferentiated cell is a stem cell.

II. Cells Involved in Keratinocyte Stem Cell Formation

In certain embodiments of the invention, there are disclosed methods and compositions for providing keratinocyte stem cells from pluripotent cells. In some embodiments, the pluripotent cells may be stem cells, including but not limited to, embryonic stem cells, fetal stem cells, adult stem cells, or induced pluripotent stem cells.

A. Stem Cells

Stem cells are cells found in most, if not all, multi-cellular organisms. They are characterized by the ability to self-renew through mitotic cell division and the ability to differentiate into a diverse range of specialized cell types. The two broad types of mammalian stem cells are embryonic stem cells that are found in blastocysts and adult stem cells that are found in adult tissues, such as keratinocyte stem cells in the epidermis. In a developing embryo, stem cells can differentiate into all of the specialized embryonic tissues. In adult organisms, stem cells and progenitor cells act as a repair system for the body, replenishing specialized cells, and also maintain the normal turnover of regenerative organs, such as blood, skin, or intestinal tissues.

Human embryonic stem cells (ESCs) and induced pluripotent stem cells (iPSCs) are capable of long-term proliferation in vitro, while retaining the potential to differentiate into all cell types of the body, including keratinocyte stem cells. Keratinocyte stem cells could potentially provide an unlimited supply of patient-specific functional keratinocyte stem cells for both drug development and therapeutic uses. The differentiation of human ESCs/iPSCs to keratinocyte stem cells in vitro recapitulates normal in vivo development, i.e. they undergo the normal sequential developmental stages. That sequential developmental process requires the addition of different growth factors and stimuli at different stages of differentiation. Certain aspects of the invention provide fully functional keratinocyte stem cells by differentiating human ESCs/iPSCs. This approach generates keratinocyte stem cells with functions highly similar, if not identical, to human primary adult keratinocytes. In addition, the keratinocyte stem cells of the invention, with their extended proliferation ability, have unique advantages as the starting cell population for keratinocyte terminal differentiation found in the super basal layers of the epidermis.

As used herein, "expression" refers to the production of a material or substance as well as the level or amount of production of a material or substance. Thus, determining the expression of a specific marker refers to detecting either the relative or absolute amount of the marker that is expressed or simply detecting the presence or absence of the marker.

As used herein, "marker" refers to any molecule that can be observed or detected. For example, a marker can include, but is not limited to, a nucleic acid, such as a transcript of a specific gene, a polypeptide product of a gene, a non-gene product polypeptide, a glycoprotein, a carbohydrate, a glycolipid, a lipid, a lipoprotein, or a small molecule.

1. Embryonic Stem Cells

Embryonic stem cells (ES cells) are pluripotent stem cells derived from the epiblast tissue of the inner cell mass of a blastocyst or earlier morula stage embryo. ES cells are distinguished by two distinctive properties: their pluripotency and their capability to self-renew indefinitely. ES cells are pluripotent, that is, they are able to differentiate into all derivatives of the three primary germ layers: ectoderm, endoderm, and mesoderm. Additionally, under defined conditions, embryonic stem cells are capable of propagating themselves indefinitely. This allows embryonic stem cells to be employed as useful tools for both research and regenerative medicine, because they can produce limitless numbers of themselves for continued research or clinical use. ES cells can develop into each of the more than 200 cell types of the adult body when given sufficient and necessary stimulation for a specific cell type. They do not, however, contribute to the extra-embryonic membranes or the *placenta*.

Nearly all research to date has taken place using mouse embryonic stem cells (mES) or human embryonic stem cells (hES). Both have the essential stem cell characteristics, yet they require very different environments in order to maintain an undifferentiated state. Mouse ES cells may be grown on a layer of gelatin and require the presence of Leukemia Inhibitory Factor (LIF). Human ES cells could be grown on a feeder layer of mouse embryonic fibroblasts (MEFs) and often require the presence of basic Fibroblast Growth Factor (bFGF or FGF-2). Without optimal culture conditions or genetic manipulation (Chambers et al., 2003), embryonic stem cells will rapidly differentiate.

A human embryonic stem cell may also be defined by the presence of several transcription factors and cell surface proteins. The transcription factors Oct-4, Nanog, and Sox-2 form the core regulatory network that ensures the suppression of genes that lead to differentiation and the maintenance of pluripotency (Boyer et al., 2005). The cell surface antigens most commonly used to identify hES cells include the glycolipids SSEA3 and SSEA4 and the keratan sulfate antigens Tra-1-60 and Tra-1-81.

Methods for obtaining mouse ES cells are well known. In one method, a preimplantation blastocyst from the 129 strain of mice is treated with mouse antiserum to remove the trophoectoderm, and the inner cell mass is cultured on a feeder cell layer of chemically inactivated mouse embryonic fibroblasts in medium containing fetal calf serum. Colonies of undifferentiated ES cells that develop are subcultured on mouse embryonic fibroblast feeder layers in the presence of fetal calf serum to produce populations of ES cells. In some methods, mouse ES cells can be grown in the absence of a feeder layer by adding the cytokine leukemia inhibitory factor (LIF) to serum-containing culture medium (Smith, 2000). In other methods, mouse ES cells can be grown in serum-free medium in the presence of bone morphogenetic protein and LIF (Ying et al., 2003).

Human ES cells can be obtained from blastocysts using previously described methods (Thomson et al., 1995; Thomson et al., 1998; Thomson and Marshall, 1998; Reubinoff et al., 2000). In one method, day-5 human blastocysts are exposed to rabbit anti-human spleen cell antiserum, and then exposed to a 1:5 dilution of Guinea pig complement to lyse trophectoderm cells. After removing the lysed trophectoderm cells from the intact inner cell mass, the inner cell mass is cultured on a feeder layer of gamma-inactivated mouse embryonic fibroblasts and in the presence of fetal bovine serum. After 9 to 15 days, clumps of cells derived from the inner cell mass can be chemically (i.e. exposed to trypsin) or mechanically dissociated and replated in fresh medium containing fetal bovine serum and a feeder layer of mouse embryonic fibroblasts. Upon further proliferation, colonies having an undifferentiated morphology are selected by micropipette, mechanically dissociated into clumps, and replated (see U.S. Pat. No. 6,833,269). ES-like morphology is characterized as compact colonies with apparently high nucleus to cytoplasm ratio and prominent nucleoli. Resulting ES cells can be routinely passaged by brief trypsinization or by selection of individual colonies by micropipette. In some methods, human ES cells can be grown without serum by culturing the ES cells on a feeder layer of fibroblasts in the presence of basic fibroblast growth factor (Amit et al., 2000). In other methods, human ES cells can be grown without a feeder cell layer by culturing the cells on a protein matrix such as Matrigel™ or laminin in the presence of "conditioned" medium containing basic fibroblast growth factor (Xu et al., 2001). The medium is previously conditioned by coculturing with fibroblasts.

Methods for the isolation of rhesus monkey and common marmoset ES cells are also known (Thomson and Marshall, 1998; Thomson et al., 1995; Thomson and Odorico, 2000).

Another source of ES cells is established ES cell lines. Various mouse cell lines and human ES cell lines are known and conditions for their growth and propagation have been defined. For example, the mouse CGR8 cell line was established from the inner cell mass of mouse strain 129 embryos, and cultures of CGR8 cells can be grown in the presence of LIF without feeder layers. As a further example, human ES cell lines H1, H7, H9, H13, and H14 were established by Thompson et al. (1995). In addition, subclones H9.1 and H9.2 of the H9 line have been developed. It is anticipated that virtually any ES or stem cell line known in the art may be used with the present invention, such as, e.g., those described in Yu and Thompson (2008), which is incorporated herein by reference.

The source of ES cells for use in connection with the present invention can be a blastocyst, cells derived from culturing the inner cell mass of a blastocyst, or cells obtained from cultures of established cell lines. Thus, as used herein, the term "ES cells" can refer to inner cell mass cells of a blastocyst, ES cells obtained from cultures of inner mass cells, and ES cells obtained from cultures of ES cell lines.

2. Induced Pluripotent Stem Cells

Induced pluripotent stem cells, commonly abbreviated as iPS cells or iPSCs, are a type of pluripotent stem cell artificially derived from a non-pluripotent cell, typically an adult somatic cell. Induced pluripotent stem cells are believed to be similar if not identical to natural pluripotent stem cells, such as embryonic stem cells in many respects, such as in terms of the expression of certain stem cell genes and proteins, chromatin methylation patterns, doubling time, embryoid body formation, teratoma formation, viable chimera formation, and potency and differentiability, but the full extent of their relation to natural pluripotent stem cells is still being assessed.

iPS cells are obtained by reprogramming of differentiated somatic cells. Generation of induced pluripotent cells derived from human tissue other than of embryonic origin is desired to alleviate ethical concerns regarding experimental use of embryos and embryonic tissue. The promise of therapeutic applications from induced pluripotent cells has been touted. Medical applications include treatments for Alzheimer's disease, diabetes and spinal cord injuries to name a few. Other applications include disease modeling and pharmaceutical drug screening.

Induced pluripotent stem cells have been obtained by various methods. Human fetal or newborn fibroblasts are transfected with four genes, Oct4, Sox2, Nanog and Lin28 using lentiviral transduction (Yu et al., 2007). At 12-20 days post infection, colonies with human ES cell morphology become visible. The colonies are picked and expanded. The induced pluripotent stem cells making up the colonies are morphologically similar to human ES cells, express various human ES cell markers, and form teratomas having neural tissue, cartilage, and gut epithelium after injection into mice.

In another method, adult human dermal fibroblasts are transfected with transcription factors Oct4, Sox2, c-Myc and Klf4 using retroviral transduction (Takahashi et al., 2007). The transfected cells are plated on SNL feeder cells (a mouse cell fibroblast cell line that produces LIF) in medium supplemented with basic fibroblast growth factor (bFGF). After approximately 25 days, colonies resembling human ES cell colonies appear in culture. The ES cell-like colonies are picked and expanded on feeder cells in the presence of bFGF.

iPS cells were first produced in 2006 (Takahashi et al., 2006) from mouse cells and in 2007 from human cells (Takahashi et al., 2007; Yu et al, 2007). This has been cited as an important advancement in stem cell research, as it may allow researchers to obtain pluripotent stem cells, which are important in research and potentially have therapeutic uses, without the controversial use of embryos. The first successful demonstration of generating induced pluripotent cells (iPS cells) from mouse or human tissue involved the use of retroviral vectors expressing a specific set of transcription factors. Research in the laboratories of James Thomson and Shinya Yamanaka has demonstrated that introduction of specific transcription factors by retroviral vectors into mouse or human fibroblasts is sufficient to reprogram those cells to undifferentiated pluripotent stems cells. The factors used by Thomson include Oct4, Sox2, Nanog and Lin28. The factors used by Yamanaka include Oct4, Sox2, Klf4 and c-Myc. Reprogramming via either gene set is accomplished by integration into the host cell genome and expression of the transcription factors or expression from episomal plasmids that can then be lost from the reprogrammed cell resulting in a scarless iPS cell.

Based on cell characteristics, cells of the ES cell-like colonies are induced pluripotent stem cells. The induced pluripotent stem cells are morphologically similar to human ES cells, and express various human ES cell markers. Also, when grown under conditions that are known to result in differentiation of human ES cells, the induced pluripotent stem cells differentiate accordingly. For example, the induced pluripotent stem cells can differentiate into cells having keratinocyte stem cell structures and markers. It is anticipated that virtually any iPS cells or cell lines may be used with the present invention, including, e.g., those described in Yu and Thompson (2008).

Methods of preparing induced pluripotent stem cells from mouse are also known (Takahashi and Yamanaka, 2006). Induction of iPS cells typically requires the expression of or exposure to at least one member from Sox family and at least one member from Oct family. Sox and Oct are thought to be central to the transcriptional regulatory hierarchy that specifies ES cell identity. For example, Sox may be Sox-1, Sox-2, Sox-3, Sox-15, or Sox-18; Oct may be Oct-4. Additional factors may increase the reprogramming efficiency, like Nanog, Lin28, Klf4, or c-Myc; specific sets of reprogramming factors may be a set comprising Sox-2, Oct-4, Nanog, and optionally, Lin-28; or comprising Sox-2, Oct4, Klf, and optionally, c-Myc.

iPS cells, like ES cells, have characteristic antigens that can be identified or confirmed by immunohistochemistry or flow cytometry, using antibodies for SSEA-1, SSEA-3 and SSEA-4 (Developmental Studies Hybridoma Bank, National Institute of Child Health and Human Development, Bethesda Md.), and TRA-1-60 and TRA-1-81 (Andrews et al., 1987). Pluripotency of iPS cells can be confirmed by injecting approximately $0.5\text{-}10 \times 10^6$ cells into the rear leg muscles of 8-12 week old male SCID mice. Teratomas develop that demonstrate at least one cell type of each of the three germ layers.

In certain aspects of the present invention, iPS cells are made from reprogramming somatic cells using reprogramming factors comprising an Oct family member and a Sox family member, such as Oct4 and Sox2 in combination with Klf and/or Nanog as described above and as described in WO2009/149233. The somatic cell for reprogramming may be any somatic cell that can be induced to pluripotency, such as a fibroblast, a keratinocyte, a hematopoietic cell, a mesenchymal cell, a liver cell, a stomach cell, or a β cell. In a certain aspect, T cells may also be used as source of somatic cells for reprogramming (see WO2010/141801, incorporated herein by reference).

Reprogramming factors may be expressed from expression cassettes comprised in one or more vectors, such as an integrating vector or an episomal vector, e.g., an EBV element-based system (see WO2009/149233, incorporated herein by reference; Yu et al., 2009). In a further aspect, reprogramming proteins could be introduced directly into somatic cells by protein transduction.

III. Keratinocyte Stem Cell Characteristics

Cells can be characterized according to a number of phenotypic criteria. The criteria include but are not limited to the detection or quantification of expressed cell markers, enzymatic activity, and the characterization of morphological features and intercellular signaling.

Keratinocyte stem cells embodied in certain aspects of this invention have morphological features characteristic of keratinocyte stem cells in nature. One or more such features present in a single cell are consistent with the cell being a member of the keratinocyte stem cell lineage. Unbiased determination of whether cells have morphologic features characteristic of keratinocyte stem cells can be made by coding micrographs of differentiated progeny cells, adult or fetal keratinocyte stem cells, and one or more negative control cells, such as a fibroblast, or melanocytes and then evaluating the micrographs in a blinded fashion, and breaking the code to determine if the keratinocyte stem cells from differentiation are accurately identified.

Cells of this invention can also be characterized according to whether they express phenotypic markers characteristic of the keratinocyte lineage. General epidermal keratinocytes are characterized as expressing cytokeratin 14 and p63. Within such a population, there are colony forming keratinocyte stem cells and keratinocyte progenitors on route to terminal differentiation. Non-limiting examples of cell markers useful in distinguishing keratinocyte stem cells, keratinocyte progenitors and more differentiated keratinocyte derivatives include cytokeratin 15, CD49f, keratin 1, loricrin, and filaggrin.

General epidermal keratinocytes and keratinocyte stem cell protein determinants listed in this disclosure can be detected using any suitable immunological technique—such as flow immunocytochemistry for cell-surface markers, immunohistochemistry (for example, of fixed cells or tissue sections) for intracellular or cell-surface markers, Western blot analysis of cellular extracts, and enzyme-linked immunoassay, for cellular extracts or products secreted into the medium. Expression of an antigen by a cell is said to be "antibody-detectable" if a significantly detectable amount of antibody will bind to the antigen in a standard immunocytochemistry or flow cytometry assay, optionally after fixation of the cells, and optionally using a labeled secondary antibody or other conjugate (such as a biotin-avidin conjugate) to amplify labeling.

The expression of specific markers can also be detected at the mRNA level by Northern blot analysis, dot-blot hybridization analysis, or by real-time polymerase chain reaction (PCR) using sequence-specific primers in standard amplification methods (U.S. Pat. No. 5,843,780). Sequence data for the particular markers listed in this disclosure can be obtained from public databases, such as GenBank. Expression at the mRNA level is said to be "detectable" according to one of the assays described in this disclosure if the performance of the assay on cell samples according to standard procedures in a typical controlled experiment results in clearly discernable hybridization or amplification product within a standard time window. Unless otherwise required, expression of a particular marker is indicated if the corresponding mRNA is detectable by RT-PCR. Expression of keratinocyte stem cell-specific markers as detected at the protein or mRNA level is considered positive if the level is at least 2-fold, and preferably more than 10- or 50-fold above that of a control cell, such as an undifferentiated pluripotent stem cell, a fibroblast, or other unrelated cell type.

In another aspect, the biological function of a keratinocyte stem cell provided by differentiation may be evaluated, for example, by colony formation assays, by determining the ability of keratinocyte stem cells to differentiate and stratify on mouse de-epidermized dermis, or by the ability of keratinocyte stem cells to engraft onto nude mice. In yet another aspect, keratinocyte stem cells may be identified by expression of cytokeratin 15 and/or CD49f. Keratinocyte stem cells may be testing using functional assays. For example, the cells may be transplanted onto the wounded epidermis of a mouse embryo to test their ability to engraft.

One advantage of culturing keratinocyte stem cells is that the cells can be grown in a homogenous undifferentiated cell population. As such, their use to generate mature lineages may result in the increased efficiency of differentiation of more specialized cell types. This also reduces the potential of unwanted effects from contaminating cell types, such as those from other germ layers. Keratinocyte stem cells of the invention can be characterized as essentially free of some or all contaminating cell types if less than 0.1% (preferably less than 100 or 10 ppm) bear markers or other features of an undesired cell type, as determined by immunostaining and fluorescence-activated quantitation, or other appropriate techniques.

Cells provided according to certain aspects of this invention can have a number of the features of cells obtained from primary sources. The more of these features that are present in a particular cell, the more it can be characterized as a cell of the keratinocyte stem cell lineage. Cells having at least 2, 3, 5, 7, or 9 of these features are increasingly more preferred. In reference to a particular cell population as may be present in a culture vessel or a preparation for administration, uniformity between cells in the expression of these features is often advantageous. In this circumstance, populations in which at least about 40%, 60%, 80%, 90%, 95%, or 98% of the cells have the desired features are increasingly more preferred.

IV. Keratinocyte Stem Cell Differentiation Factors

Certain aspects of the invention provide keratinocyte stem cell differentiation factors. The inventors also contemplate that all the isoforms and variants of the growth factors and compounds listed in this section are included in this invention.

Keratinocyte stem cell promoting growth factors illustrated in this disclosure may include soluble growth factors (peptide hormones, cytokines, ligand-receptor complexes, and other compounds) that are capable of promoting the growth of keratinocyte stem cells. Non-limiting examples of such agents include, but are not limited to, growth factors, such as acidic FGF (FGF1), BMP-4, EGF, or isoforms or variants thereof.

Differentiation to provide keratinocyte stem cells may be accomplished by contacting cells with an effective amount of any one or more of the factors described in this section, including, but not limited to, BMP4, fibroblast growth factor (e.g., FGF1), epidermal growth factor (e.g., EGF), ascorbic acid, cholera toxin, nicotinamide, a cyclic AMP analogue (e.g., 8-Br-cAMP), a TGFβ RI Kinase Inhibitor II (TG-FRKi), and retinoic acid (e.g., all-trans RA). An "effective amount" is an amount sufficient to effect beneficial or desired results. An effective amount can be administered in one or more administrations. An effective amount of the can be an amount that is sufficient to promote expansion or differentiation of keratinocyte stem cells. The concentrations of the factors can range from about 0.01 ng/mL to about 500 μg/mL, preferably from about 0.1 ng/mL to about 500 ng/mL, most preferably from about 1 ng/mL to 100 ng/mL.

V. Cell Culture

The starting cell and the differentiated cell generally have differing requirements for culture medium and conditions. It is usual to carry out at least an initial stage of culture, after introduction of the differentiation factors, in the presence of medium and under culture conditions known to be suitable for growth of the starting cell. This is followed by a subsequent period of culture in the presence of a differentiation medium and under conditions known to be suitable for the differentiated cell. After a sufficient time for differentiation, the differentiated cells may be further cultured for expansion of the differentiated cells in an expansion medium. Such an expansion medium may comprise one or more signaling inhibitors as described above or comprise a culture medium essentially free of these inhibitors.

The initial stage of culture is preferably for a period of up to 6 days, more preferably up to 4 days and in particular embodiments, described below for not more than 3 days, and more particularly up to or about one day. The subsequent stage of culture in differentiation medium comprising one or more signaling inhibitors is suitably for a period of at least or about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33 days, or any range derivable therein, and can be for a period of up to 120 days, preferably up to 10 days. In a specific embodiment described below used to generate keratinocyte stem cells, the initial stage of culture was for a period of about 5 days and the subsequent stages were for about 26 to 44 days by culture in the presence of various differentiation media. The differentiation conditions may be essentially free of feeder cells. In further aspects, the differentiation medium may be chemically defined. To improve differentiation, the differentiation medium may further comprise high concentration of FGF and may be essentially free of TGF-β. In some instances, the medium may comprise TGF-β3.

A. General Conditions

The culturing conditions according to the present invention will be appropriately defined depending on the medium and stem cells used. The medium according to certain aspects of the present invention can be prepared using a medium used for culturing animal cells as its basal medium, such as any of TeSR, Essential 8 medium, BME, BGJb, CMRL 1066, Glasgow MEM, Improved MEM Zinc Option, IMDM, Medium 199, Eagle MEM, αMEM, DMEM, Ham, RPMI 1640, and Fischer's media, as well as any combinations thereof, but the medium is not particularly limited thereto as far as it can be used for culturing animal cells.

The medium according to the present invention can be a serum-containing or serum-free medium. The serum-free medium refers to media with no unprocessed or unpurified serum, and accordingly can include media with purified blood-derived components or animal tissue-derived components (such as growth factors). From the aspect of preventing contamination with heterogeneous animal-derived components, serum can be derived from the same animal as that of the stem cell(s).

The medium according to the present invention may contain or may not contain any alternatives to serum. The alternatives to serum can include materials that appropriately contain albumin (such as lipid-rich albumin, albumin substitutes such as recombinant albumin, plant starch, dextrans and protein hydrolysates), transferrin (or other iron transporters), fatty acids, insulin, collagen precursors, trace elements, 2-mercaptoethanol, 3'-thiolgiycerol, or equivalents thereto. The alternatives to serum can be prepared by the method disclosed in International Publication No. 98/30679, for example. Alternatively, any commercially available materials can be used for more convenience. The commercially available materials include knockout Serum Replacement (KSR), Chemically-defined Lipid concentrated (Gibco), and Glutamax (Gibco).

The medium of the present invention can also contain fatty acids or lipids, amino acids (such as non-essential amino acids), vitamin(s), growth factors, cytokines, antioxidant substances, 2-mercaptoethanol, pyruvic acid, buffering agents, and inorganic salts. The concentration of 2-mercaptoethanol can be, for example, about 0.05 to 1.0 mM, and particularly about 0.1 to 0.5 mM, but the concentration is particularly not limited thereto as long as it is appropriate for culturing the stem cell(s).

A culture vessel used for culturing the cell(s) of the present invention can include, but is particularly not limited to: flask, flask for tissue culture, dish, petri dish, dish for tissue culture, multi dish, micro plate, micro-well plate, multi plate, multi-well plate, micro slide, chamber slide, tube, tray, CellSTACK® Chambers, culture bag, and roller bottle, as long as it is capable of culturing the cells therein. The stem cells may be cultured in a volume of at least or about 0.2, 0.5, 1, 2, 5, 10, 20, 30, 40, 50 ml, 100 ml, 150 ml, 200 ml, 250 ml, 300 ml, 350 ml, 400 ml, 450 ml, 500 ml, 550 ml, 600 ml, 800 ml, 1000 ml, 1500 ml, or any range derivable therein, depending on the needs of the culture. In a certain embodiment, the culture vessel may be a bioreactor, which may refer to any device or system that supports a biologically active environment. The bioreactor may have a volume of at least or about 2, 4, 5, 6, 8, 10, 15, 20, 25, 50, 75, 100, 150, 200, 500 liters, 1, 2, 4, 6, 8, 10, 15 cubic meters, or any range derivable therein.

The culture vessel can be cellular adhesive or non-adhesive and selected depending on the purpose. The cellular adhesive culture vessel can be coated with any of substrates for cell adhesion such as extracellular matrix (ECM) to improve the adhesiveness of the vessel surface to the cells. The substrate for cell adhesion can be any material intended to attach stem cells or feeder cells (if used). The substrate for cell adhesion includes collagen, gelatin, poly-L-lysine, poly-D-lysine, vitronectin, laminin, fibronectin, PLO laminin, fibrin, thrombin, and RetroNectin and mixtures thereof, for example, Matrigel™, and lysed cell membrane preparations (Klimanskaya et al., 2005).

Other culturing conditions can be appropriately defined. For example, the culturing temperature can be about 30-40° C., for example, at least or about 31, 32, 33, 34, 35, 36, 37, 38, 39° C. but particularly not limited to them. The $CO_2$ concentration can be about 1 to 10%, for example, about 2 to 5%, or any range derivable therein. The oxygen tension can be at least or about 1, 5, 8, 10, 20%, or any range derivable therein. The oxygen tension is preferably 20% for normoxic cultures.

The methods of the present invention in certain aspects can be used for adhesion culture of cells, for example. In this case, the cells can be cultured in the presence of feeder cells. In the case where the feeder cells are used in the methods of the present invention, stromal cells such as fetal fibroblasts can be used as feeder cells (for example, refer to; Hogan et al., Manipulating the Mouse Embryo, A Laboratory Manual (1994); Gene Targeting, A Practical Approach (1993); Martin (1981); Evans and Kaufman (1981); Jainchill et al., (1969); Nakano et al. (1996); Kodama et al. (1982); and International Publication Nos. 01/088100 and 2005/080554).

The methods of the present invention in certain aspects can also be used for a suspension culture of cells, including suspension culture on carriers (Fernandes et al., 2004) or gel/biopolymer encapsulation (U.S. Publication 2007/0116680). The term suspension culture of the cells means that the cells are cultured under non-adherent condition with respect to the culture vessel or feeder cells (if used) in a medium. The suspension culture of cells includes a dissociation culture of cells and an aggregate suspension culture of cells. The term dissociation culture of cells means that suspended cells are cultured, and the dissociation culture of cells include those of single cells or those of small cell aggregates composed of a plurality of cells (for example, about 2 to 400 cells). When the aforementioned dissociation culture is continued, the cultured, dissociated cells form a larger aggregate of cells, and thereafter an aggregate suspension culture can be performed. The aggregate suspension culture includes an embryoid culture method (see Keller et al., 1995), and a SFEB method (Watanabe et al., 2005; International Publication No. 2005/123902).

The culture vessel used for culturing cells in suspension according to the method of some embodiments of the invention can be any tissue culture vessel with a suitable purity grade having an internal surface designed such that cells cultured therein are unable to adhere or attach to such a surface (e.g., non-tissue culture treated cells, to prevent attachment or adherence to the surface). Preferably, in order to obtain a scalable culture, culturing according to some embodiments of the invention is effected using a controlled culturing system (preferably a computer-controlled culturing system) in which culture parameters such as temperature, agitation, pH, and $pO_2$ is automatically performed using a suitable device. Once the culture parameters are recorded, the system is set for automatic adjustment of culture parameters as needed for promotion of cell expansion. Cells may be cultured under dynamic conditions (i.e., under conditions in which the cells are subject to constant movement while in the suspension culture) or under non-dynamic conditions (i.e., a static culture) while preserving their proliferative capacity. For non-dynamic culturing of cells, the cells can be cultured in uncoated 58 mm Petri dishes (Greiner, Frickenhausen, Germany). For dynamic culturing of cells, the cells can be cultured in spinner flasks (e.g., of 200 ml to 1000 ml, for example 250 ml; of 100 ml; or in 125 ml Erlenmeyer) which can be connected to a control unit and thus present a controlled culturing system. The culture vessel (e.g., a spinner flask, an Erlenmeyer) is shaken continuously. According to some embodiments of the invention the culture vessels are shaken at 15 revolutions per minute (rpm) using a shaker. According to some embodiments of the invention the culture medium is changed daily.

B. Culturing Pluripotent Stem Cells

Cultures of pluripotent stem cells are described as "undifferentiated" when a substantial proportion of stem cells and their derivatives in the population display morphological characteristics of undifferentiated cells, clearly distinguishing them from differentiated cells of embryo or adult origin. Undifferentiated ES or iPS cells are recognized by those skilled in the art, and typically appear in the two dimensions of a microscopic view in colonies of cells with high nuclear/cytoplasmic ratios and prominent nucleoli. It is understood that colonies of undifferentiated cells can have neighboring cells that are differentiated.

ES cells can be maintained in an undifferentiated state by culturing the cells in the presence of serum and a feeder layer, typically mouse embryonic fibroblasts. Other methods for maintaining stem cells in an undifferentiated state are also known. For example, mouse ES cells can be maintained in an undifferentiated state by culturing in the presence of LIF without a feeder layer. However, unlike mouse ES cells, pre-existing human ES cells do not respond to LIF. Human ES cells can be maintained in an undifferentiated state by culturing ES cells on a feeder layer of fibroblasts in the presence of basic fibroblast growth factor (Amit et al., 2000), or by culturing on a protein matrix, such as Matrigel™ or laminin, without a feeder layer and in the presence of fibroblast-conditioned medium plus basic fibroblast growth factor (Xu et al., 2001; U.S. Pat. No. 6,833,269).

Methods for preparing and culturing ES cells can be found in standard textbooks and reviews in cell biology, tissue culture, and embryology, including teratocarcinomas and embryonic stem cells: A practical approach (1987); Guide to Techniques in Mouse Development (1993); Embryonic Stem Cell Differentiation in vitro (1993); Properties and uses of Embryonic Stem Cells: Prospects for Application to Human Biology and Gene Therapy (1998), all incorporated herein by reference. Standard methods used in tissue culture generally are described in Animal Cell Culture (1987); Gene Transfer Vectors for Mammalian Cells (1987); and Current Protocols in Molecular Biology and Short Protocols in Molecular Biology (1987 & 1995).

After somatic cells are introduced or contacted with reprogramming factors, these cells may be cultured in a medium sufficient to maintain the pluripotency and the undifferentiated state. Culturing of induced pluripotent stem (iPS) cells generated in this invention can use various medium and techniques developed to culture primate pluripotent stem cells, more specially, embryonic stem cells, as described in U.S. Pat. Publications 2007/0238170, 2003/0211603, and 2008/0171385, which are hereby incorporated by reference. It is appreciated that additional methods for the culture and maintenance of pluripotent stem cells, as would be known to one of skill, may be used with the present invention.

In certain embodiments, undefined conditions may be used; for example, pluripotent cells may be cultured on fibroblast feeder cells or a medium that has been exposed to fibroblast feeder cells in order to maintain the stem cells in an undifferentiated state.

Alternately, pluripotent cells may be cultured and maintained in an essentially undifferentiated state using defined, feeder-independent culture system, such as a TeSR medium (Ludwig et al., 2006a; Ludwig et al., 2006b) or Essential 8 medium (Chen et al., 2011). Feeder-independent culture systems and media may be used to culture and maintain pluripotent cells. These approaches allow derived human iPS cells as well as human embryonic stem cells to remain in an essentially undifferentiated state without the need for mouse fibroblast "feeder layers." As described herein, various modifications may be made to these methods in order to reduce costs as desired.

Various matrix components may be used in culturing and maintaining human pluripotent stem cells. For example, Matrigel™, collagen IV, fibronectin, laminin, PLO laminin, collagenI, collagenIV, fibrin clot, and vitronectin in combination may be used to coat a culturing surface as a means of providing a solid support for pluripotent cell growth, as described in Ludwig et al. (2006a; 2006b), which are incorporated by reference in their entirety. Particularly, Matrigel™ may be used to provide a substrate for cell culture and maintenance of human pluripotent stem cells. Matrigel™ is a gelatinous protein mixture secreted by mouse tumor cells and is commercially available from BD Biosciences (New Jersey, USA). This mixture resembles the complex extracellular environment found in many tissues and is used by cell biologists as a substrate for cell culture.

C. Cell Passaging

Certain aspects of the present invention can further involve a step of dissociating cells. Cell dissociation can be performed using any known procedures. These procedures include treatments with a chelating agent (such as EDTA), an enzyme (such as trypsin, collagenase), or the like, and operations such as mechanical dissociation (such as pipetting). The cell(s) can be treated with the ROCK inhibitor or myosin II inhibitor before and/or after dissociation. For example, the cell(s) may be treated only after dissociation.

In some further embodiments of cell culturing, once a culture container is full, the colony may be split into aggregated cells or even single cells by any method suitable for dissociation, which cells are then placed into new culture containers for passaging. Cell passaging is a technique that enables one to keep cells alive and growing under cultured conditions for extended periods of time. Cells usually would be passed when they are about 70%-100% confluent.

Single-cell dissociation of cells followed by single cell passaging may be used in the present methods with several advantages, like facilitating cell expansion, cell sorting, and defined seeding for differentiation and enabling automation of culture procedures and clonal expansion. For example, progeny cell clonally derivable from a single cell may be homogenous in genetic structure and/or synchronized in cell cycle, which may increase targeted differentiation. Exemplary methods for single cell passaging may be as described in U.S. Pat. Publication 2008/0171385, which is incorporated herein by reference.

In certain embodiments, cells may be dissociated into single individual cells, or a combination of single individual cells and small cell clusters comprising 2, 3, 4, 5, 6, 7, 8, 9, 10 cells or more. The dissociation may be achieved by mechanical force, or by a cell dissociation agent, such as sodium citrate, or an enzyme, for example, trypsin, trypsin-EDTA, TrypLE Select, or the like.

Based on the source of cells and the need for expansion, the dissociated cells may be transferred individually or in small clusters to new culture containers in a splitting ratio such as at least or about 1:2, 1:4, 1:5, 1:6, 1:8, 1:10, 1:20, 1:40, 1:50, 1:100, 1:150, 1:200, or any range derivable therein. Suspension cell line split ratios may be done on volume of culture cell suspension. The passage interval may be at least or about every 1, 2, 3, 4, 5, 6, 7, 8, 9, 10, 11, 12, 13, 14, 15, 16, 17, 18, 19, 20 days or any range derivable therein. For example, the achievable split ratios for the different enzymatic passaging protocols may be 1:2 every 3-7 days, 1:3 every 4-7 days, and 1:5 to 1:10 approximately every 7 days, 1:50 to 1:100 every 7 days. When high split ratios are used, the passage interval may be extended to at least 12-14 days or any time period without cell loss due to excessive spontaneous differentiation or cell death.

In certain aspects, single cell passaging may be in the presence of a small molecule effective for increasing cloning efficiency and cell survival, such as a ROCK inhibitor as described above. Such a ROCK inhibitor, e.g., Y-27632, HA-1077, H-1152, HA-100, or blebbistatin, may be used at an effective concentration, for example, at least or about 0.02, 0.05, 0.1, 0.2, 0.5, 1, 2, 3, 4, 5, 10, 15, 20, 25, 30, 35, 40, 45, 50 to about 100 µM, or any range derivable therein.

VI. Expression of Markers

To determine the amount of a specific cell type in a cell culture or cell population, a method of distinguishing the specific cell type from the other cells in the culture or in the population is desirable. Accordingly, markers whose presence, absence, and/or relative expression levels are specific for certain cell types made according to the present invention are provided as are methods for detecting and determining the expression of such markers.

The presence, absence, and/or level of expression of a marker may be determined by quantitative PCR (qPCR). For example, the amount of transcript produced by certain genetic markers, such as cytokeratin 14, cytokeratin 15, P63, or CD49f, is determined by quantitative qPCR. Additionally, immunohistochemistry or flow cytometry may be used to detect the proteins expressed by the above-mentioned genes. qPCR, flow cytometry, and immunohistochemistry may be used to identify and determine the amount or relative proportions of such markers.

VII. Use of Keratinocyte Stem Cells

The keratinocyte stem cells provided by methods and compositions of certain aspects of the invention can be used in a variety of applications. These include but are not limited to transplantation or implantation of the keratinocyte stem cells in vivo; screening cytotoxic compounds, carcinogens, mutagens growth/regulatory factors, pharmaceutical compounds, etc., in vitro; studying the mechanism by which drugs and/or growth factors operate; gene therapy; and the production of biologically active products, to name but a few.

A. Test Compound Screening

Keratinocyte stem cells of this invention and keratinocytes-derived therefrom can be used to screen for factors (such as solvents, small molecule drugs, peptides, and polynucleotides) or environmental conditions (such as culture conditions or manipulation) that affect the characteristics of keratinocytes provided herein.

In some applications, stem cells (differentiated or undifferentiated) are used to screen factors that promote maturation of cells along the keratinocyte lineage, or promote proliferation and maintenance of such cells in long-term culture. For example, candidate keratinocyte maturation factors or growth factors are tested by adding them to keratinocyte stem cells in different wells, and then determining any phenotypic change that results, according to desirable criteria for further culture and use of the cells.

Particular screening applications of this invention relate to the testing of pharmaceutical compounds in drug research and cosmetic testing. The reader is referred generally to the standard textbook *In vitro Methods in Pharmaceutical Research*, Academic Press, 1997, and U.S. Pat. No. 5,030, 015). In certain aspects of this invention, cells differentiated to the keratinocyte lineage play the role of test cells for standard drug screening and toxicity assays, as have been previously performed on keratinocyte cell lines or primary keratinocyte cells in short-term culture. Assessment of the activity of candidate pharmaceutical compounds generally involves combining the keratinocyte cells provided in certain aspects of this invention with the candidate compound, determining any change in the morphology, marker phenotype, or metabolic activity of the cells that is attributable to the compound (compared with untreated cells or cells treated with an inert compound), and then correlating the effect of the compound with the observed change. The screening may be done either because the compound is designed to have a pharmacological effect on keratinocytes, or because a compound designed to have effects elsewhere may have unintended side effects on keratinocytes. Two or more drugs can be tested in combination (by combining with the cells either simultaneously or sequentially), to detect possible drug-drug interaction effects. In some applications, compounds are screened for toxicity to keratinocytes. See, e.g., Kuzuya et al., 2001.

B. Epithelial Sheet Generation and Transplantation

This invention also provides for the use of keratinocytes provided herein to restore a degree of epithelial function to a subject needing such therapy, perhaps due to a wound. For example, keratinocytes and keratinocyte stem cells derived by methods disclosed here may be used to treat a burn (such as, e.g., by engineering of grafts).

To determine the suitability of keratinocytes provided herein for therapeutic applications, the cells can first be tested in a suitable animal model. At one level, cells may be assessed for their ability to differentiate and stratify into skin cells by inoculating de-epidermized dermis from, for example, a mouse, as in Example 1, or a human corpse. At another level, the cells may be assessed for their ability to survive and maintain their phenotype in vivo. Keratinocytes provided herein may be administered to immunodeficient animals (such as nude mice, or animals rendered immunodeficient chemically or by irradiation) at a site amenable for further observation. For example, a portion of full-thickness skin is surgically removed from the back of the nude mice followed by insertion of a silicon dome chamber underneath the surrounding skin. Fibroblasts and keratinocytes are applied to the wound through a hole in the top of the dome. Several weeks after surgery, grafting sites are analyzed for healing of the initial wound. Tissues may be harvested after a period of several weeks or more, and assessed as to whether starting cell types, such as pluripotent stem cells are still present. This can be performed by providing the administered cells with a detectable label (such as green fluorescent protein, or β-galactosidase); or by measuring a constitutive marker specific for the administered cells. Where keratinocytes provided herein are being tested in a rodent model, the presence and phenotype of the administered cells can be assessed by immunohistochemistry or ELISA using human-specific antibody, or by RT-PCR analysis using primers and hybridization conditions that cause amplification to be specific for human polynucleotide sequences. Suitable markers for assessing gene expression at the mRNA or protein level are provided in elsewhere in this disclosure.

Keratinocytes provided by methods of the invention may be tested in various animal models for their ability to heal epidermal wounds. Keratinocytes may be mixed with skin fibroblasts and engrafted onto a skin wound, and if the cells are functional then the wound will at least partially heal. This assay is commonly used to test the function of primary keratinocytes.

Keratinocytes provided in certain aspects of this invention that demonstrate desirable functional characteristics according to their profile of enzymes, or efficacy in animal models, may also be suitable for direct administration to human subjects in need thereof. Keratinocytes may also be administered to the cornea.

A corneal epithelial sheet of the present invention may be used as transplantation material (substitute for the corneal epithelium) to a patient with damaged cornea. In transplantation, it is preferable that a graft is fixed to and allowed to survive by fixing it to the surrounding tissue with a surgical suture. Furthermore, it is preferable that after transplantation, the surface of the transplanted part is protected by temporarily being covered with a therapeutic contact lens. A corneal epithelial sheet may comprise a cell layer formed on a collagen layer, which is provided in addition to the cell layer. The collage layer may be derived from the amniotic membrane. A corneal epithelial sheet having a collagen layer may be obtained by seeding predetermined cells on the collagen layer as a substrate and culturing them.

The keratinocyte stem cells provided in certain aspects of this invention can be used for therapy of any subject in need thereof. A preferred human condition that may be appropriate for such therapy is a burn. The ultimate responsibility for determining the mode of treatment and the appropriate dose lies with the managing clinician.

Certain aspects of the invention include keratinocytes or keratinocyte stem cells provided herein that form part of a bioengineered tissue graft. Such a tissue graft may be an epithelial sheet graft.

Green and collaborators described a method for culturing human epidermal keratinocytes (Rheinwald and Green, 1975), that has been extended to other cultured epithelial cells. Under such culture conditions, stratified epithelial sheets suitable for transplantation onto large burn surfaces, ulcerations and other skin wounds are obtained (Gallico et al., 1984; Heighten et al., 1986). The cultured epithelia obtained through this procedure have also been used as allografts for temporary wound dressing (Phillips et al., 1989; Bolivar-Flores et al., 1990). Epithelial cell cultures have become a powerful tool for body surface reconstruction.

The limited shelf-life of epithelial sheets has restricted their use to those medical facilities that are not too far away from the production facility. After dispase detachment of epithelial sheets for transportation to the hospital, shelf-life is short. Therefore, the establishment of a preservation method for the cultured sheets should permit their banking and also, their shipment worldwide. In this regard, some strategies have been attempted. Several authors have developed cryopreservation methods based on the use of glycerol or dimethyl sulfoxide as cryoprotectants, following a specific freezing protocol (see U.S. Pat. No. 5,298,417). Others have cryopreserved cultured epithelial sheets with media containing both cell-penetrating glass-forming agents (specifically glycerol) and non-penetrating protectant agents (preferably polyvinylpyrrolidone (PVP), dextran or hydroxyethyl starch) (see U.S. Pat. No. 5,145,770). Still others have cryopreserved cultured epithelial sheets without the need to wash away cryopreservation components and with the option of dry preservation (see U.S. Pat. No. 6,548,297).

Sheets of keratinocytes are then transplanted back to the mammal from which the iPS cells were generated.

C. Distribution for Commercial, Therapeutic, and Research Purposes

For purposes of manufacture, distribution, and use, the keratinocyte lineage cells, including keratinocyte stem cells, of this invention are typically supplied in the form of a cell culture or suspension in an isotonic excipient or culture medium, optionally frozen to facilitate transportation or storage.

This invention also includes different reagent systems, comprising a set or combination of cells that exist at any time during manufacture, distribution, or use. The cell sets comprise any combination of two or more cell populations described in this disclosure, exemplified but not limited to differentiation-derived cells (keratinocyte lineage cells, their precursors and subtypes), in combination with undifferentiated stem cells or other differentiated cell types. The cell populations in the set sometimes share the same genome or a genetically modified form thereof. Each cell type in the set may be packaged together, or in separate containers in the same facility, or at different locations, at the same or different times, under control of the same entity or different entities sharing a business relationship.

VIII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Figure 2A:
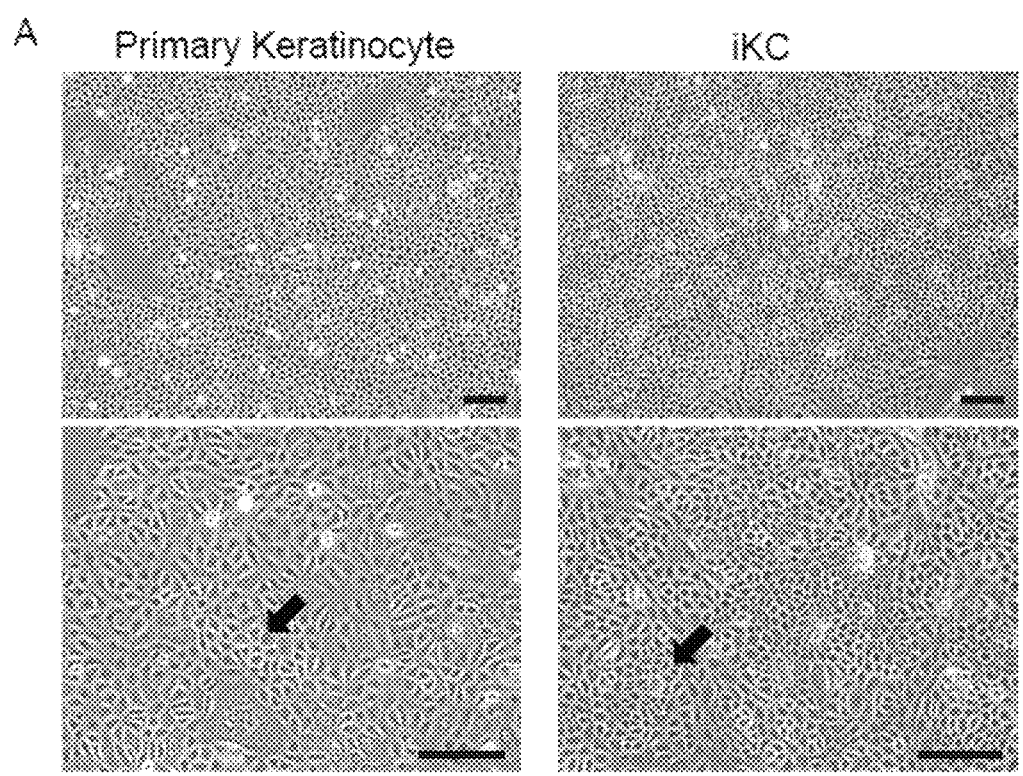
FIGS. 2A-B. Microscopic characterization of iKCs. (A) Phase-contrast microscopic images of Passage 3 human foreskin keratinocytes and Passage 1 iKCs. Arrows point to bright boundaries among cells, a typical characteristic of keratinocytes sharing tight junctions to provide the barrier function of the skin. (B) Immunofluorescence microscopic images of human foreskin keratinocytes and iKCs. Cells were fixed with 2% formaldehyde on culturing plates and stained with anti-cytokeratin 14 (K14) and -cytokeratin 15 (K15) antibodies. Images were taken under an Olympus IX71 inverted microscope in separate fluorescence channels. Scale bars, 100 µM.
Figure 2B:
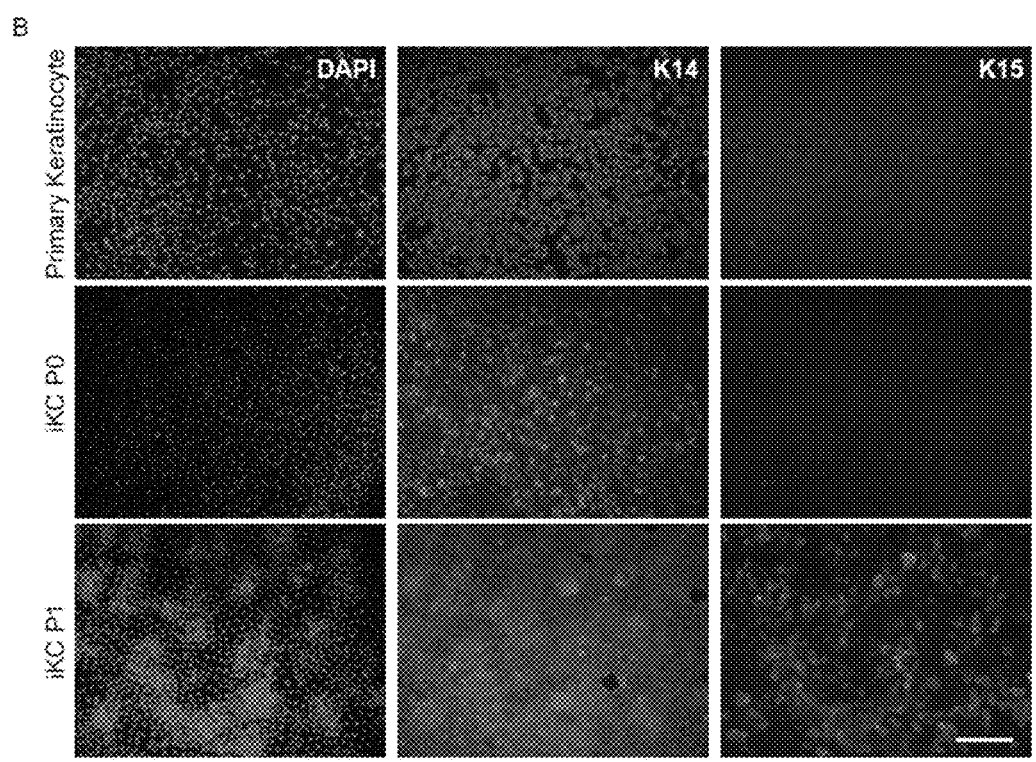

Example 1—Differentiation of Functional Keratinocytes from Pluripotent Stem Cells Keratinocyte stem cells can be generated from human ESC/iPSCs in four steps: Initiation, Differentiation, Maturation, and Maintenance (FIG. 1). At the Initiation step (Days 0-3), ESC/iPSCs aggregates were induced toward an ectodermal fate by the synergic actions of all-trans retinoic acid (RA) and neuronal fate suppressor BMP4. On Day 0, hESC/iPSCs were harvested and individualized from ~50% confluent surface culture with Accutase digestion for 5 minutes at 37° C. Single cells were washed once with mTeSR medium and plated in ultra low attachment T25 flasks at $0.7 \times 10^6$ cells/mL in 5 mL TeSR medium supplemented with myosin light chain kinase inhibitor HA-100 (10 μM). The T25 flasks were placed on a Belly Dancer agitator at 15 rpm in a 5% $CO_2$ cell culture incubator. On Day 1, hESC/iPSC aggregates were washed with initiation medium (Table 1) once, and incubated with 5 mL initiation medium from Day 1 to Day 3 with daily medium changes. At the Differentiation step (Days 4-14), committed simple epithelial precursors became cytokeratin 14 (K14)- and p63-positive keratinocyte progenitors by continuous exposure to EGF, FGF1, Ascorbic Acid, Cholera Toxin, 8-Br-cAMP, TGFβ RI Kinase Inhibitor II (TGFRKi), and a high concentration of Niacinamide. On Day 4, epithelial aggregates from T25 flasks were collected in differentiation medium (Table 2) and incubated with Accutase for 20 minutes at 37° C. Partially digested aggregates were washed with differentiation medium once and plated on Vitronectin- or Laminin-coated Nunclon 6-well plates at a density of ~20 aggregates per well. Cells were fed with differentiation medium every two days. On Day 15, keratinocyte progenitors (K14+) were passaged with 0.1% Trypsin in Versene digestion for two minutes and plated at 50,000 cells per well on Gelatin- or Laminin-coated Nunclon 6-well plates in maturation medium (Table 3). After that, keratinocyte progenitors were continuously cultured under maturation conditions (Days 15-20, Passage 1) to express keratinocyte stem cell marker cytokeratin 15 (K15) and CD49f at high levels. Once keratinocyte stem cells were generated, a moderate growth condition (Table 4) was applied at the maintenance step (Day 20+) to grow and expand the cells. Complete formulations of chemically defined culture medium (FBS- and BSA-free) at each step are provided in Tables 1-4.

iKCs were characterized microscopically and found to be more compact and individual iKCs were smaller in size compared to primary keratinocytes (FIG. 2A). Flow analysis of iKCs also suggested that iKCs were smaller than primary keratinocytes. Phase-contrast images of passage 3 human foreskin keratinocytes and passage 1 iKCs revealed bright boundaries among cells, a typical characteristic of keratinocytes sharing tight junctions to provide the barrier function of the skin (FIG. 2A). Immunofluorescent imaging of human foreskin keratinocytes and iKCs showed that cultured primary keratinocytes (P3) expressed K14 in the cytoplasm but lost K15 expression (FIG. 2B). At P0, iKCs expressed K14 at different levels but not K15; at P1, iKCs expressed K14 more homogeneously, and a fraction of the cells expressed K15, the keratinocyte stem cell marker, at high levels.

Figure 3A:
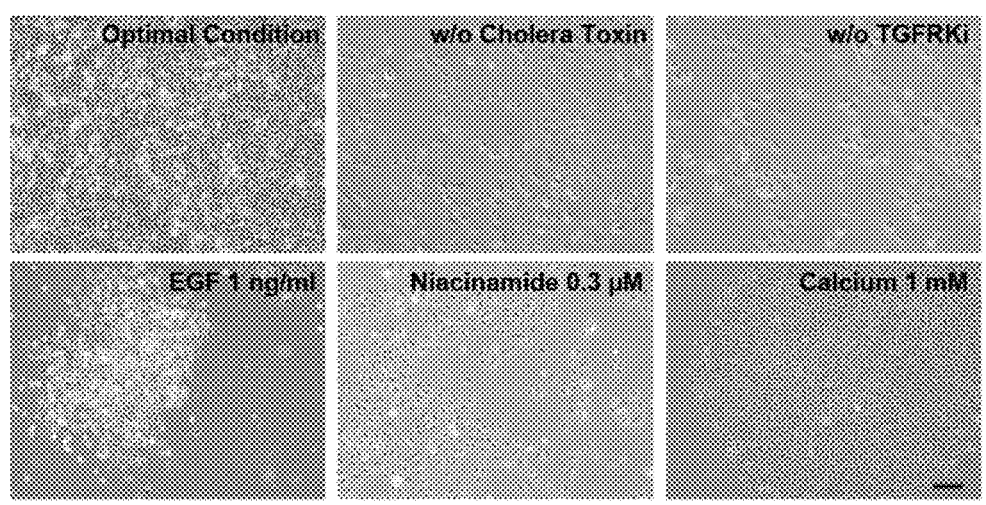
FIGS. 3A-B. Critical components for iKCs derivations. (A) Phase-contrast microscopic images of Passage 0, Day 14 differentiation culture obtained in optimal condition (see, FIG. 1 and Tables 1-2) and other non-optimal conditions with one component of the medium modified at a time. (B) Phase-contrast and immunofluorescence microscopic images of Passage 0, Day 14 differentiation culture using different fibroblast growth factors (FGFs). Cells were fixed with 2% formaldehyde on culturing plates and stained with anti-K14 antibody with DAPI DNA counterstain. Images were taken under an Olympus IX71 inverted microscope in separate fluorescence channels. Scale bars, 100 µM.
Figure 3B:
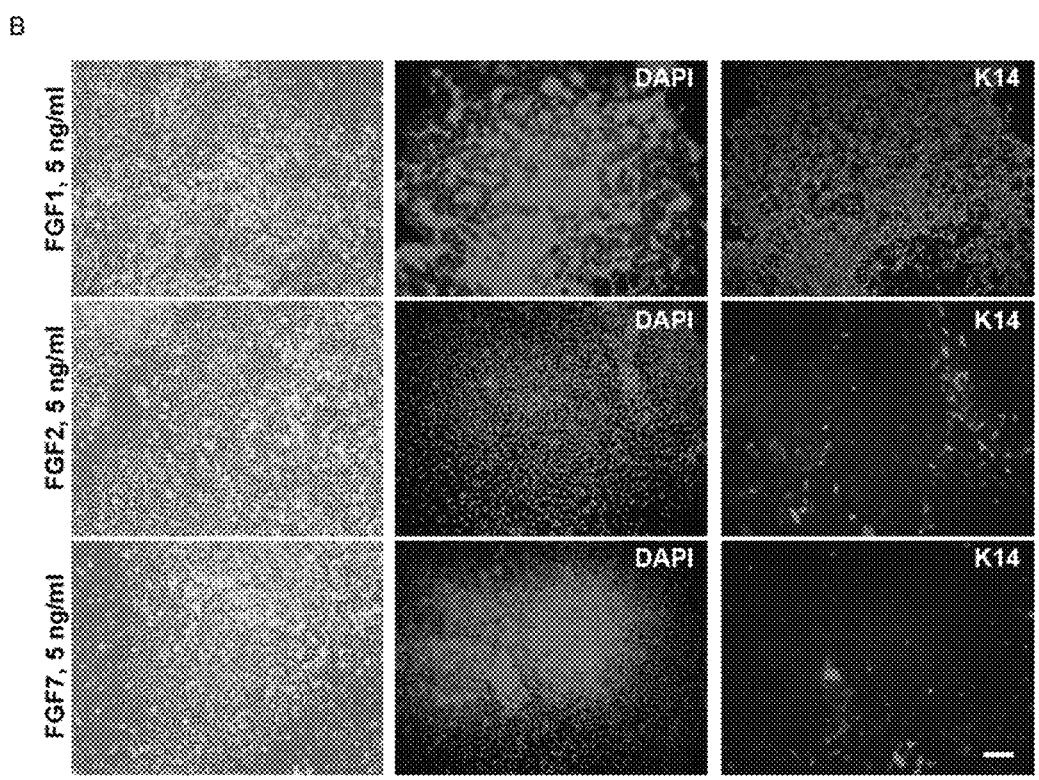

Experiments were performed to identify the critical components for iKCs derivation. First, passage 0, Day 14 differentiation cultures were obtained in optimal conditions (described in FIG. 1 and Tables 1-2) and various non-optimal conditions with one component of the medium modified at a time. The resulting cultures were imaged using phase-contrast (FIG. 3A). It was found that without Cholera toxin and TGFRKi in the media, iKCs cannot be derived efficiently. In addition, when EGF and Niacinamide concentrations were not sufficient, the differentiation process was incomplete. Similarly, when medium calcium levels were too high (at 1 mM), simple epithelial progenitors would not further differentiate into keratinocytes. Next, passage 0, Day 14 differentiation cultures were obtained using different fibroblast growth factors (FGFs). The resulting cultures were imaged by immunofluorescent staining with an anti-K14 antibody. FGF1 was found to efficiently direct cells to express mature keratinocyte marker K14, while FGF2 and FGF7 did not promote homogeneous K14 expression (FIG. 3B).

Figure 4:
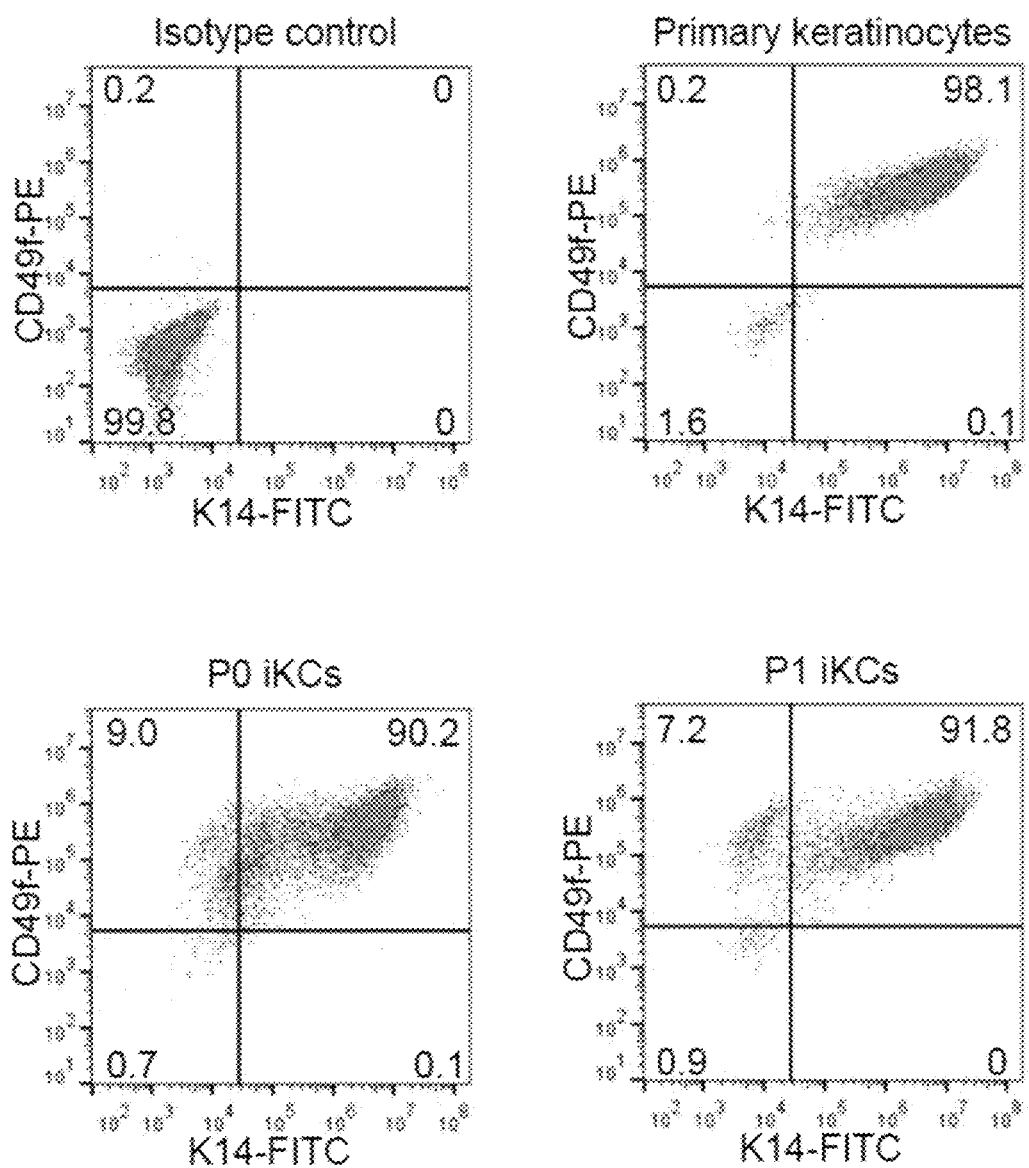
FIG. 4. Purity of iKCs differentiated from human ESC/iPSCs. iKCs were generated from the method described in FIG. 1 and harvested at the end of Passage 0 (P0) and Passage 1 (P1). Cells were fixed with 2% formaldehyde, and stained with anti-K14-FITC and anti-CD49f-PE antibodies. Stained iKCs, as well as isotype control and Passage 3 primary human foreskin keratinocytes, were analyzed on an Accuri flow cytometer.

In order to assess the purity of keratinocytes differentiated from human ESC/iPSCs, keratinocytes were generated from the method described in FIG. 1 and harvested at the end of Passage 0 (P0) and Passage 1 (P1). The resulting cultures, as well as Passage 3 primary human foreskin keratinocytes, were stained with anti-K14-FITC and anti-CD49f-PE antibodies and by flow cytometry. Positive control primary keratinocyte results showed 98.1% K14+/CD49f+ cells, consistent with basal layer keratinocyte expression profiles (FIG. 4). iKCs flow analyses at the end of P0 and P1 showed 90.2% and 91.8% K14+/CD49f+ cells, respectively. These results indicate that high purity keratinocytes expressing K14 and CD49f were generated using the differentiation protocol described in FIG. 1.

In order to determine the proliferative potential of iKCs in maintenance conditions, iKCs were passaged with 0.1% Trypsin in Versene onto gelatin-coated Nunclon E-well plates at 50,000 cells per well. Cells were fed with maintenance medium every other day and passaged again on the fifth day of each plating. Total cell numbers were recorded at each passaging to calculate population doubling numbers. The iKCs were able to be passaged five times before reaching senescence (FIG. 5A). The total number of population doubling achieved for iKCs was 11.6.

In order to determine the stemness of iKCs, colony formation assays (CFA) were performed. Cells were plated at 250 cells per well on a 6-well plate, and allowed to grow for two weeks. For primary keratinocytes, blank non-cell culture treated plates were used for optimal growth; while for iKCs, plates that were previously used to culture primary keratinocytes were used so as to have the natural Laminin deposits as the basement membrane. At the end of culture, cells were fixed with 2% formaldehyde and stained with Hoechst. Whole plates were imaged with a Molecular Devices ImageXpress high content imager. Results showed that primary keratinocytes formed ~15 distinctive big colonies which originated from the scarce keratinocyte stem cells in the general keratinocyte population (FIG. 5B). iKCs expanded a great extent during the culture period but exhibited a more homogeneous growth potential among cells (FIG. 5B). At Passage 1 (P1), iKCs grew to almost full confluency within two weeks in the colony formation assays.

The ability of iKCs to differentiate and stratify on mouse de-epidermized dermis (DED) was studied. The generate DED, back skin was surgically removed from newborn mice and cut into round pieces of ~1 cm$^2$. Skin tissues were then incubated in Versene overnight at 4° C. to loosen the connection between the epidermis and dermis. After 12 hours of incubation, the epidermis was removed with tweezers. The remaining dermis was rinsed with 70% ethanol and PBS, each with three repeats. Clean dermis was then processed through liquid nitrogen freezing and thawing at room temperature for 10 cycles to devitalize the tissue. The resulting tissue was transferred to PBS with 1% Penstrep at 4° C. for 24 hours. At this point, the DED may be immediately used or may be stored at −20° C. To seed cells on DED, the DEDs were taken out of PBS and dipped into keratinocyte maintenance medium. Cells of interest were lifted from the surface culture with Trypsin and collected in maintenance medium. About one million cells were resuspended in ~100 μl maintenance medium. DEDs were first placed on the top chamber of the Transwell (Corning); cell suspensions were then applied gently on top of the DEDs. Cells were allowed to settle for five minutes. DED-grafts were fed from the bottom of the transwell with 1.5 mL maintenance medium for two weeks. Maintenance medium was changed every other day. After two weeks of culture in transwells, DED-grafts were lifted and embedded in OCT compound for cryosectioning. Sections (16 μM) were cut and stained with Haematoxylin, so that grafted cells would show pink staining for their nucleus. The DED grafting results showed that Passage 1 iKCs were able to differentiate on the mouse DED and form stratified layers similar to the primary human keratinocytes (FIG. 6A).

Next, iKCs were tested for their ability to engraft on the back of FoxN1 nude mice. FoxN1 immunodeficient nude mice were anesthetized by isofluorane inhalation. A round portion ~1 cm$^2$ of full-thickness skin (epidermis and dermis) was surgically removed from the back of the nude mice, where a silicon dome chamber was snuggly inserted underneath the surrounding skin secured by the contraction at the wound. The silicon dome chamber not only provided a humid environment for grafted cells to survive and grow, but also prevented surrounding autologous skin from spreading and healing the wound. One million dermal fibroblasts (FBs) and one million keratinocytes (KCs) were suspended in 150 μl DMEM, and applied gently to the center of the wound through a hole on the top of the dome. Isofluorane was removed after 10 minutes from the time when cells were grafted. Mice were housed individually and fed with painkiller chow for the first four days post surgery. One week after the surgery, the silicon chamber was removed from the wound. Three weeks after the surgery, mice were euthanized to analyze the grafting sites. Pictures taken at three weeks post surgery showed that iKCs (2 replicates) were able to cover and heal the initial wound on the skin to a similar extent as primary mouse and human keratinocytes (FIG. 6B). Of note, the iKC grafts lacked residual hair because they were free of hair follicle stem cells that are often found in the primary keratinocytes.

TABLE 1

Formulation of initiation medium for iKCs differentiation.

| | MW | μM |
|---|---|---|
| Amino Acids | | |
| Glycine | 75 | 100 |
| L-Alanine | 89 | 100 |
| L-Arginine hydrochloride | 211 | 1000 |
| L-Asparagrine-H2O | 150 | 100 |
| L-Aspartic acid | 133 | 30 |
| L-Carnitine HCl | 197 | 50 |
| L-Cysteine hydrochloride-H2O | 176 | 240 |
| L-Glutamic acid | 147 | 100 |
| L-Glutamine | 146 | 6000 |
| L-Histidine hydrochloride-H$_2$O | 210 | 280 |
| L-Isoleucine | 131 | 470 |
| L-Leucine | 131 | 500 |
| L-Lysine hydrochloride | 183 | 100 |
| L-Methionine | 149 | 82 |
| L-Phenylalanine | 165 | 77 |
| L-Proline | 115 | 300 |
| L-Serine | 105 | 600 |
| L-Threonine | 119 | 170 |
| L-Tryptophan | 204 | 27 |
| L-Tyrosine disodium salt dehydrate | 261 | 52 |
| L-Valine | 117 | 300 |
| Vitamins | | |
| Biotin | 244 | 0.06 |
| Choline chloride | 140 | 100 |
| D-Calcium pantothenate | 238 | 2 |
| Folic acid | 441 | 1.8 |
| Niacinamide | 122 | 0.3 |
| Pyridoxine hydrochloride | 206 | 0.3 |
| Riboflavin | 376 | 0.1 |
| Thiamine hydrochloride | 337 | 1 |
| Vitamin B12 | 1355 | 0.3 |
| i-Inositol | 180 | 100 |
| Inorganic salts | | |
| Ammonium Metavanadate | 117 | 0.005 |
| Ammonium Molybdate | 1236 | 0.001 |
| Calcium Chloride (CaCl$_2$) (anhyd.) | 111 | 90 |
| Cupric sulfate (CuSO$_4$—5H$_2$O) | 250 | 0.011 |
| Ferric sulfate (FeSO$_4$—7H$_2$O) | 278 | 5 |
| Magnesium chloride (anhyd.) | 95 | 600 |
| Manganese sulfate (MnSO$_4$—H$_2$O) | 169 | 0.001 |
| Nickelous chloride (NiCl$_2$ 6H$_2$O) | 238 | 0.0005 |
| Potassium chloride (KCl) | 75 | 1500 |
| Sodium bicarbonate (NaHCO$_3$) | 84 | 14000 |
| Sodium chloride (NaCl) | 58 | 121500 |
| Sodium Meta Silicate (NaSiO$_3$ 9H$_2$O) | 261 | 0.5 |
| Sodium phosphate dibasic | 142 | 2000 |
| Sodium selenite anhyd. (Na$_2$SeO$_3$) | 173 | 0.022 |
| Stanium chloride (SnCl$_2$ 2H$_2$O) | 226 | 0.0005 |
| Zinc sulfate (ZnSO$_4$—7H$_2$O) | 288 | 0.5 |

TABLE 1-continued

Formulation of initiation medium for iKCs differentiation.

|  | MW | µM |
|---|---|---|
| Others |  |  |
| Thymidine | 242 | 3 |
| Adenine HCl | 171.6 | 180 |
| D-Glucose (Dextrose) | 180 | 6000 |
| Lipoic Acid | 206 | 1 |
| Phenol Red HCl | 376 | 3.3 |
| HEPES | 238 | 25180 |
| Putrescine 2HCl | 161 | 1 |
| Sodium pyruvate | 110 | 500 |
| Sodium acetate | 82 | 3670 |
| Active differentiation factors |  |  |
| 8-Bromo-cAMP | 430 | 200 |
| Cholera toxin | 84000 | 0.0001 |
| Ascorbic acid | 172 | 174 |
| Triiodothyronine | 651 | 0.01 |
| Ethanolamine | 61 | 100 |
| Phosphorylethanolamine | 141 | 100 |
| Apo-Transferrin | 76000 | 0.066 |
| Hydrocortisone | 362 | 0.552 |
| All-trans Retinoic acid | 300 | 1 |
| Insulin | 5808 | 0.0172 |
| BMP4 | 34000 | 7.35E−04 |
| FGF1 | 15800 | 3.16E−04 |
| EGF | 3400 | 1.56E−02 |
| IGF1 | 7655 | 1.31E−03 |

TABLE 2

Formulation of differentiation medium for iKCs differentiation.

|  | MW | µM |
|---|---|---|
| Amino Acids |  |  |
| Glycine | 75 | 100 |
| L-Alanine | 89 | 100 |
| L-Arginine hydrochloride | 211 | 1000 |
| L-Asparagrine-H2O | 150 | 100 |
| L-Aspartic acid | 133 | 30 |
| L-Carnitine HCl | 197 | 50 |
| L-Cysteine hydrochloride-H2O | 176 | 240 |
| L-Glutamic acid | 147 | 100 |
| L-Glutamine | 146 | 6000 |
| L-Histidine hydrochloride-H$_2$O | 210 | 280 |
| L-Isoleucine | 131 | 470 |
| L-Leucine | 131 | 500 |
| L-Lysine hydrochloride | 183 | 100 |
| L-Methionine | 149 | 82 |
| L-Phenylalanine | 165 | 77 |
| L-Proline | 115 | 300 |
| L-Serine | 105 | 600 |
| L-Threonine | 119 | 170 |
| L-Tryptophan | 204 | 27 |
| L-Tyrosine disodium salt dehydrate | 261 | 52 |
| L-Valine | 117 | 300 |
| Vitamins |  |  |
| Biotin | 244 | 0.06 |
| Choline chloride | 140 | 100 |
| D-Calcium pantothenate | 238 | 2 |
| Folic acid | 441 | 1.8 |
| Niacinamide | 122 | 0.3 |
| Pyridoxine hydrochloride | 206 | 0.3 |
| Riboflavin | 376 | 0.1 |
| Thiamine hydrochloride | 337 | 1 |
| Vitamin B12 | 1355 | 0.3 |
| i-Inositol | 180 | 100 |
| Inorganic salts |  |  |
| Ammonium Metavanadate | 117 | 0.005 |
| Ammonium Molybdate | 1236 | 0.001 |

TABLE 2-continued

Formulation of differentiation medium for iKCs differentiation.

|  | MW | µM |
|---|---|---|
| Calcium Chloride (CaCl$_2$) (anhyd.) | 111 | 90 |
| Cupric sulfate (CuSO$_4$—5H$_2$O) | 250 | 0.011 |
| Ferric sulfate (FeSO$_4$—7H$_2$O) | 278 | 5 |
| Magnesium chloride (anhyd.) | 95 | 600 |
| Manganese sulfate (MnSO$_4$—H$_2$O) | 169 | 0.001 |
| Nickelous chloride (NiCl$_2$ 6H$_2$O) | 238 | 0.0005 |
| Potassium chloride (KCl) | 75 | 1500 |
| Sodium bicarbonate (NaHCO$_3$) | 84 | 14000 |
| Sodium chloride (NaCl) | 58 | 121500 |
| Sodium Meta Silicate (NaSiO$_3$ 9H$_2$O) | 261 | 0.5 |
| Sodium phosphate dibasic | 142 | 2000 |
| Sodium selenite anhyd. (Na$_2$SeO$_3$) | 173 | 0.022 |
| Stanium chloride (SnCl$_2$ 2H$_2$O) | 226 | 0.0005 |
| Zinc sulfate (ZnSO$_4$—7H$_2$O) | 288 | 0.5 |
| Others |  |  |
| Thymidine | 242 | 3 |
| Adenine HCl | 171.6 | 180 |
| D-Glucose (Dextrose) | 180 | 6000 |
| Lipoic Acid | 206 | 1 |
| Phenol Red HCl | 376 | 3.3 |
| HEPES | 238 | 25180 |
| Putrescine 2HCl | 161 | 1 |
| Sodium pyruvate | 110 | 500 |
| Sodium acetate | 82 | 3670 |
| Active differentiation factors |  |  |
| 8-Bromo-cAMP | 430 | 200 |
| Cholera toxin | 84000 | 0.0001 |
| Ascorbic acid | 172 | 174 |
| Triiodothyronine | 651 | 0.01 |
| Ethanolamine | 61 | 100 |
| Phosphorylethanolamine | 141 | 100 |
| Apo-Transferrin | 76000 | 0.066 |
| Hydrocortisone | 362 | 0.552 |
| Insulin | 5808 | 0.0172 |
| FGF1 | 15800 | 3.16E−04 |
| EGF | 6400 | 1.56E−02 |
| IGF1 | 7655 | 1.31E−03 |
| TGFRKi (Day 10-14) | 287.3 | 1 |
| Niacinamide (Day 8-14) | 122 | 3000 |

TABLE 3

Formulation of maturation medium for iKCs differentiation.

|  | MW | µM |
|---|---|---|
| Amino Acids |  |  |
| Glycine | 75 | 100 |
| L-Alanine | 89 | 100 |
| L-Arginine hydrochloride | 211 | 1000 |
| L-Asparagrine-H2O | 150 | 100 |
| L-Aspartic acid | 133 | 30 |
| L-Carnitine HCl | 197 | 50 |
| L-Cysteine hydrochloride-H2O | 176 | 240 |
| L-Glutamic acid | 147 | 100 |
| L-Glutamine | 146 | 6000 |
| L-Histidine hydrochloride-H$_2$O | 210 | 280 |
| L-Isoleucine | 131 | 470 |
| L-Leucine | 131 | 500 |
| L-Lysine hydrochloride | 183 | 100 |
| L-Methionine | 149 | 82 |
| L-Phenylalanine | 165 | 77 |
| L-Proline | 115 | 300 |
| L-Serine | 105 | 600 |
| L-Threonine | 119 | 170 |
| L-Tryptophan | 204 | 27 |
| L-Tyrosine disodium salt dehydrate | 261 | 52 |
| L-Valine | 117 | 300 |

TABLE 3-continued

Formulation of maturation medium for iKCs differentiation.

| | MW | µM |
|---|---|---|
| Vitamins | | |
| Biotin | 244 | 0.06 |
| Choline chloride | 140 | 100 |
| D-Calcium pantothenate | 238 | 2 |
| Folic acid | 441 | 1.8 |
| Niacinamide | 122 | 0.3 |
| Pyridoxine hydrochloride | 206 | 0.3 |
| Riboflavin | 376 | 0.1 |
| Thiamine hydrochloride | 337 | 1 |
| Vitamin B12 | 1355 | 0.3 |
| i-Inositol | 180 | 100 |
| Inorganic salts | | |
| Ammonium Metavanadate | 117 | 0.005 |
| Ammonium Molybdate | 1236 | 0.001 |
| Calcium Chloride ($CaCl_2$) (anhyd.) | 111 | 90 |
| Cupric sulfate ($CuSO_4$—$5H_2O$) | 250 | 0.011 |
| Ferric sulfate ($FeSO_4$—$7H_2O$) | 278 | 5 |
| Magnesium chloride (anhyd.) | 95 | 600 |
| Manganese sulfate ($MnSO_4$—$H_2O$) | 169 | 0.001 |
| Nickelous chloride ($NiCl_2$ $6H_2O$) | 238 | 0.0005 |
| Potassium chloride (KCl) | 75 | 1500 |
| Sodium bicarbonate ($NaHCO_3$) | 84 | 14000 |
| Sodium chloride (NaCl) | 58 | 121500 |
| Sodium Meta Silicate ($NaSiO_3$ $9H_2O$) | 261 | 0.5 |
| Sodium phosphate dibasic | 142 | 2000 |
| Sodium selenite anhyd. ($Na_2SeO_3$) | 173 | 0.022 |
| Stanium chloride ($SnCl_2$ $2H_2O$) | 226 | 0.0005 |
| Zinc sulfate ($ZnSO_4$—$7H_2O$) | 288 | 0.5 |
| Others | | |
| Thymidine | 242 | 3 |
| Adenine HCl | 171.6 | 180 |
| D-Glucose (Dextrose) | 180 | 6000 |
| Lipoic Acid | 206 | 1 |
| Phenol Red HCl | 376 | 3.3 |
| HEPES | 238 | 25180 |
| Putrescine 2HCl | 161 | 1 |
| Sodium pyruvate | 110 | 500 |
| Sodium acetate | 82 | 3670 |
| Active differentiation factors | | |
| 8-Bromo-cAMP | 430 | 200 |
| Cholera toxin | 84000 | 0.0001 |
| Ascorbic acid | 172 | 5.833333 |
| Triiodothyronine | 651 | 0.01 |
| Ethanolamine | 61 | 100 |
| Phosphorylethanolamine | 141 | 100 |
| Apo-Transferrin | 76000 | 0.066 |
| Hydrocortisone | 362 | 0.552 |
| Insulin | 5808 | 0.0172 |
| FGF1 | 15800 | 3.16E−04 |
| EGF | 6400 | 1.56E−03 |
| IGF1 | 7655 | 1.31E−03 |
| VEGF | 19165 | 1.30E−03 |
| Niacinamide | 122 | 3000 |

TABLE 4

Formulation of maintenance medium for iKCs.

| | MW | µM |
|---|---|---|
| Amino Acids | | |
| Glycine | 75 | 100 |
| L-Alanine | 89 | 100 |
| L-Arginine hydrochloride | 211 | 1000 |
| L-Asparagrine-H2O | 150 | 100 |
| L-Aspartic acid | 133 | 30 |
| L-Carnitine HCl | 197 | 50 |
| L-Cysteine hydrochloride-H2O | 176 | 240 |
| L-Glutamic acid | 147 | 100 |
| L-Glutamine | 146 | 6000 |
| L-Histidine hydrochloride-$H_2O$ | 210 | 280 |
| L-Isoleucine | 131 | 470 |
| L-Leucine | 131 | 500 |
| L-Lysine hydrochloride | 183 | 100 |
| L-Methionine | 149 | 82 |
| L-Phenylalanine | 165 | 77 |
| L-Proline | 115 | 300 |
| L-Serine | 105 | 600 |
| L-Threonine | 119 | 170 |
| L-Tryptophan | 204 | 27 |
| L-Tyrosine disodium salt dehydrate | 261 | 52 |
| L-Valine | 117 | 300 |
| Vitamins | | |
| Biotin | 244 | 0.06 |
| Choline chloride | 140 | 100 |
| D-Calcium pantothenate | 238 | 2 |
| Folic acid | 441 | 1.8 |
| Niacinamide | 122 | 0.3 |
| Pyridoxine hydrochloride | 206 | 0.3 |
| Riboflavin | 376 | 0.1 |
| Thiamine hydrochloride | 337 | 1 |
| Vitamin B12 | 1355 | 0.3 |
| i-Inositol | 180 | 100 |
| Inorganic salts | | |
| Ammonium Metavanadate | 117 | 0.005 |
| Ammonium Molybdate | 1236 | 0.001 |
| Calcium Chloride ($CaCl_2$) (anhyd.) | 111 | 90 |
| Cupric sulfate ($CuSO_4$—$5H_2O$) | 250 | 0.011 |
| Ferric sulfate ($FeSO_4$—$7H_2O$) | 278 | 5 |
| Magnesium chloride (anhyd.) | 95 | 600 |
| Manganese sulfate ($MnSO_4$—$H_2O$) | 169 | 0.001 |
| Nickelous chloride ($NiCl_2$ $6H_2O$) | 238 | 0.0005 |
| Potassium chloride (KCl) | 75 | 1500 |
| Sodium bicarbonate ($NaHCO_3$) | 84 | 14000 |
| Sodium chloride (NaCl) | 58 | 121500 |
| Sodium Meta Silicate ($NaSiO_3$ $9H_2O$) | 261 | 0.5 |
| Sodium phosphate dibasic | 142 | 2000 |
| Sodium selenite anhyd. ($Na_2SeO_3$) | 173 | 0.022 |
| Stanium chloride ($SnCl_2$ $2H_2O$) | 226 | 0.0005 |
| Zinc sulfate ($ZnSO_4$—$7H_2O$) | 288 | 0.5 |
| Others | | |
| Thymidine | 242 | 3 |
| Adenine HCl | 171.6 | 180 |
| D-Glucose (Dextrose) | 180 | 6000 |
| Lipoic Acid | 206 | 1 |
| Phenol Red HCl | 376 | 3.3 |
| HEPES | 238 | 25180 |
| Putrescine 2HCl | 161 | 1 |
| Sodium pyruvate | 110 | 500 |
| Sodium acetate | 82 | 3670 |
| Active differentiation factors | | |
| 8-Bromo-cAMP | 430 | 200 |
| Cholera toxin | 84000 | 0.0001 |
| Triiodothyronine | 651 | 0.01 |
| Ethanolamine | 61 | 100 |
| Phosphorylethanolamine | 141 | 100 |
| Apo-Transferrin | 76000 | 0.066 |
| Hydrocortisone | 362 | 0.552 |
| Insulin | 5808 | 0.0172 |
| FGF1 | 15800 | 3.16E−04 |
| EGF | 6400 | 1.56E−04 |
| IGF1 | 7655 | 1.31E−03 |
| VEGF | 19165 | 1.30E−03 |
| Niacinamide | 122 | 3000 |
| TGFRKi (Day 10-14) | 287.3 | 0.1 |

TABLE 5

Efficiency of keratinocyte stem cell differentiation from H1 ESCs.

| Input H1 ESCs on Day 0 | Output Keratinocytes on Day 14 | Efficiency |
|---|---|---|
| 3,500,000 | 44,640,000 | 12.75 |
| 3,500,000 | 31,680,000 | 9.05 |
| 3,500,000 | 48,240,000 | 13.78 |
|  |  | Avg 11.86 ± 2.49 |

TABLE 6

Amino acid supplements.

| KCM Basal | Final Concentration (mg/L) |
|---|---|
| Histidine | 47.68 |
| Isoleucine | 67.548 |
| Methionine | 13.48 |
| Phenylalanine | 13.96 |
| Threonine | 21.91 |
| Tryptophan | 6.12 |
| Tyrosine | 10.39 |

TABLE 7

Growth factor and small molecule supplements for defined human primary keratinocyte culture media (KCM).

| Component | Concentration | KCM1 | KCM2 | KCM3 | KCM4 |
|---|---|---|---|---|---|
| Calcium | 0.08 mM | 0.08 mM | 0.08 mM | 0.08 mM | 0.08 mM |
| EOP | 0.1 mM | 0.1 mM | 0.1 mM | 0.1 mM | 0.1 mM |
| Transferrin | 5 µg/mL | 5 µg/mL | 5 µg/mL | 5 µg/mL | 5 µg/mL |
| Hydrocortisone | 0.2 µg/mL | 0.2 µg/mL | 0.2 µg/mL | 0.2 µg/mL | 0.2 µg/mL |
| FGF1 | 1 ng/mL | 1 ng/mL | 1 ng/mL | 1 ng/mL | 1 ng/mL |
| EGF | 0.5 ng/mL | 0.5 ng/mL | 0.5 ng/mL | 0.5 ng/mL | 0.5 ng/mL |
| IGF | 0-10 ng/mL | 10 ng/mL | 10 ng/mL | 10 ng/mL | 10 ng/mL |
| T3 | 0-10 nM |  | 10 nM | 10 nM | 10 nM |
| L-Carnitine HCl | 0-5 µM |  | 5 µM | 5 µM | 5 µM |
| 8-Br-cAMP | 0-0.2 mM |  | 0.2 mM | 0.2 mM | 0.2 mM |
| Cholera Toxin | 0-100 pM |  | 100 pM | 100 pM | 100 pM |
| Niacinamide | 0-3 mM |  |  | 3 mM | 3 mM |
| BMP4 | 0-0.5 ng/mL |  |  |  | 0.5 ng/mL |
| VEGF | 0-25 ng/mL |  |  |  |  |
| Insulin | 0-10 µg/mL |  |  |  |  |

Example 2—Expansion and Maintenance of Primary Keratinocytes

Provided here is a chemically defined medium for the expansion and maintenance of primary human keratinocytes. With this medium, primary keratinocytes can be expanded for 40+ population doublings while maintaining their colony formation ability. The medium may also be used for the differentiation of human ESC/iPSCs to keratinocyte-like cells for both in vitro and in vivo applications.

The chemically defined media for the culture of primary human keratinocytes (KCM, keratinocyte culture medium) uses MCDB 153 as a basal medium, which was supplemented with additional amino acids (Table 6). The complete medium was also supplemented with calcium (80 µM), EOP (ethanolamine and phosphorylethanolamine both at 0.1 mM), transferrin (5 µg/mL), hydrocortisone (0.2 µg/mL), FGF1 (1 ng/mL), EGF (0.5 ng/mL) and IGF1 (10 ng/mL). The following components were tested in different medium formulations to optimize primary keratinocyte culture (Table 7): T3 (10 nM), L-carnitine HCl (5 µM), 8-Br-cAMP (0.2 mM), cholera toxin (100 µM), niacinamide (3 mM), BMP4 (0.5 ng/mL), VEGF (25 ng/mL) and insulin (0-10 µg/mL, in addition to or in place of IGF, as indicated).

Three metrics were used to assess the functionality of cells grown in the various media: morphology, population doubling, and colony formation assay (CFA).

Figure 7A:
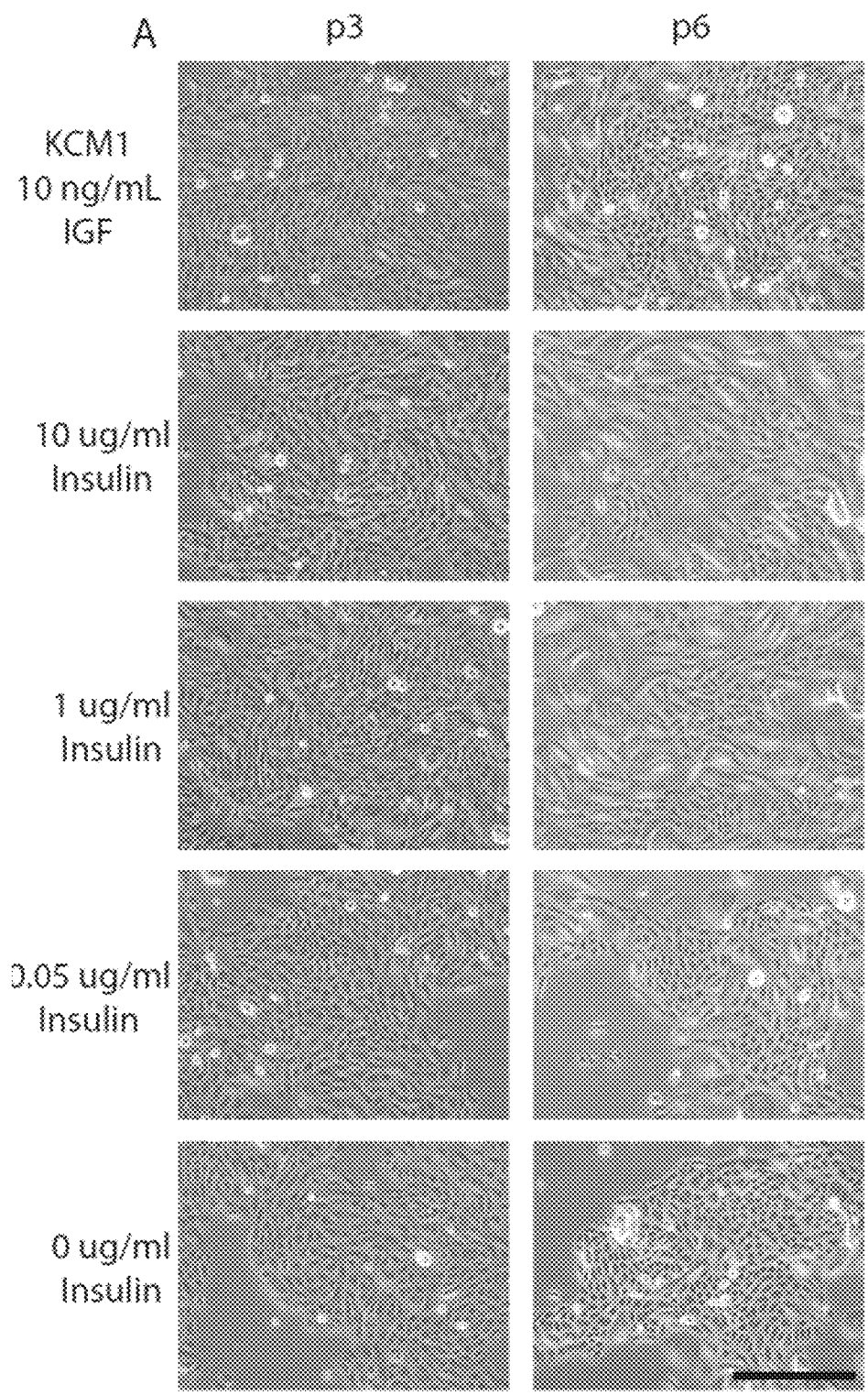

Studies were performed to determine the effect of insulin and IGF on keratinocyte growth. Cells grew well at all concentrations of insulin, including 0 µg/mL. However, keratinocytes grown in high concentrations of insulin (1 µg/mL and higher) had many larger, differentiated cells at later passages (p6), while cells grown in IGF and low concentrations of insulin (0.05 µg/mL and 0 µg/mL) were smaller and appear to be more tightly attached to each other (FIG. 7A). Furthermore, in long-term culture of primary keratinocytes in KCM1, the growth rate of cells cultured with IGF was similar to cells grown with insulin (FIG. 7B). CFAs of keratinocytes cultured in KCM1 variations were performed with the cells being switched from the indicated culture medium to KCM1 (10 µg/mL insulin) at the beginning of the CFA. Keratinocytes were cultured in KCM1 (10 µg/mL insulin) for 12 days and colony size was measured. Cells grown in KCM1 supplemented with either IGF or insulin performed similarly in the CFA (FIG. 7C). There were no statistically significant differences for any of the conditions for either colony number or size.

Figure 8A:
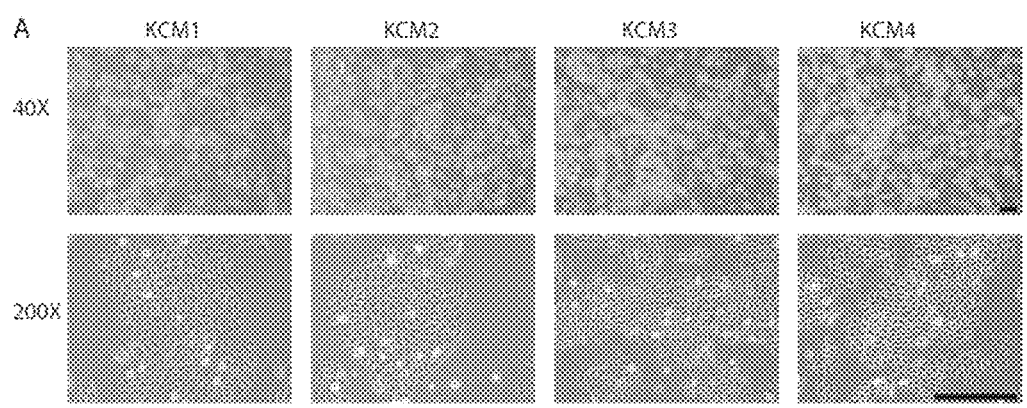

The effect of niacinamide and BMP-4 on the life span of primary keratinocytes in culture was determined. Keratinocytes grown in KCM1, KCM2, KCM3, and KCM4 on non-coated plastic plates all exhibited a colony growth pattern typical of keratinocytes (FIG. 8A). The addition of niacinamide (KCM3 and KCM4) made the cells smaller, a phenotype associated with keratinocyte stem cells. Furthermore, in long-term culture of primary keratinocytes in different media formulations was studied (FIG. 8B). KCM1, the simplest formulation, supported keratinocyte growth for ~12 population doublings. The addition of T3, L-carnitine, 8-Br-cAMP, and cholera toxin to the medium (KCM2) increased the number of cell doublings to ~19. Niacinamide (KCM3) provided a further boost in proliferative potential and increased the population doublings to ~26. BMP4 (KCM4) also significantly increased the number of population doublings (~40). CFAs of keratinocytes (P4) cultured in different media formulations were performed. The components that increased the number of population doublings also increased colony number and size in CFAs (FIGS. 8C-E). The keratinoctyes grown in KCM4 maintained the ability to form colonies through passage 9 (~35 population doublings) in CFAs. BMP4 and niacinamide were found to be key components of KCM4 responsible for the extension of lifespan and maintenance of colony formation ability, i.e., BMP4 and niacinamide maintained the stemness of primary keratinocyte stem cells in culture.

Figure 9C:
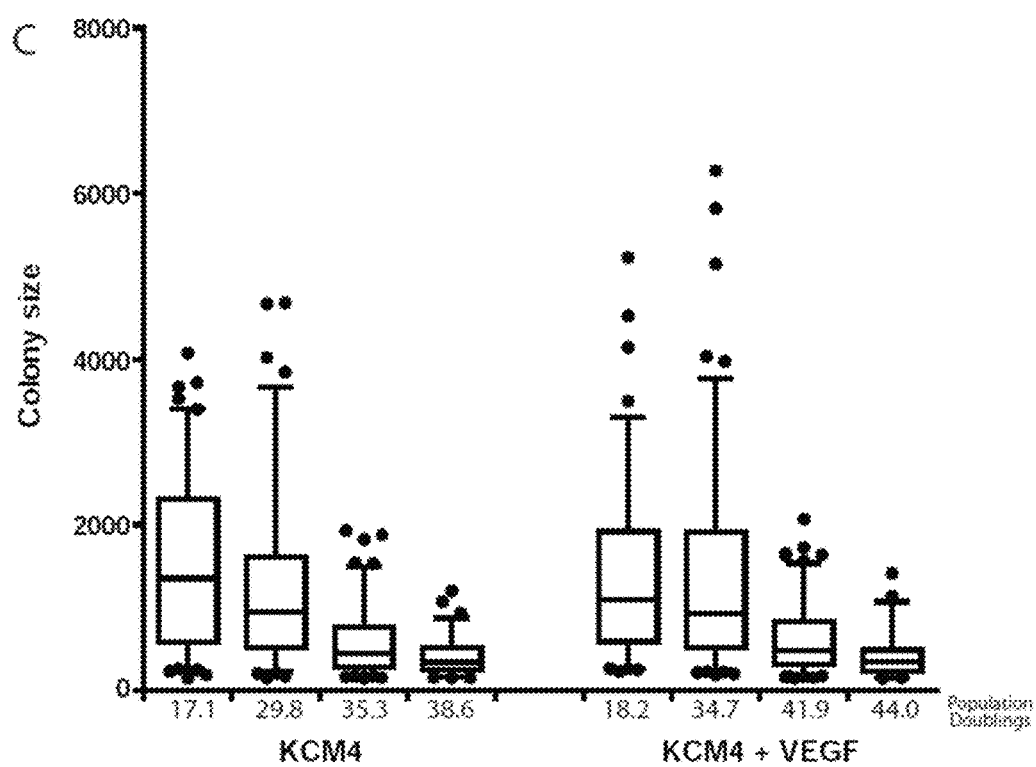

The effect of VEGF on the proliferative potential of primary keratinocytes was determined. In long-term culture of primary keratinocytes grown in KCM4 and KCM4+VEGF (25 ng/mL), the addition of VEGF to KCM4 medium did not show any morphological differences but did increase the proliferative potential of keratinocytes (FIG. 9A). Moreover, VEGF was found to have a positive effect in CFAs in later passages. For example, at ~35 population doublings (P10 for KCM4 and P8 for KCM4+VEGF) the average KCM4 colony size was 585 units while the average KCM4+VEGF colony size was 1370 units (FIG. 9B). Of note, KCM4 needed to be supplemented with 5 µg/mL insulin to support colony growth.

Figure 10C:
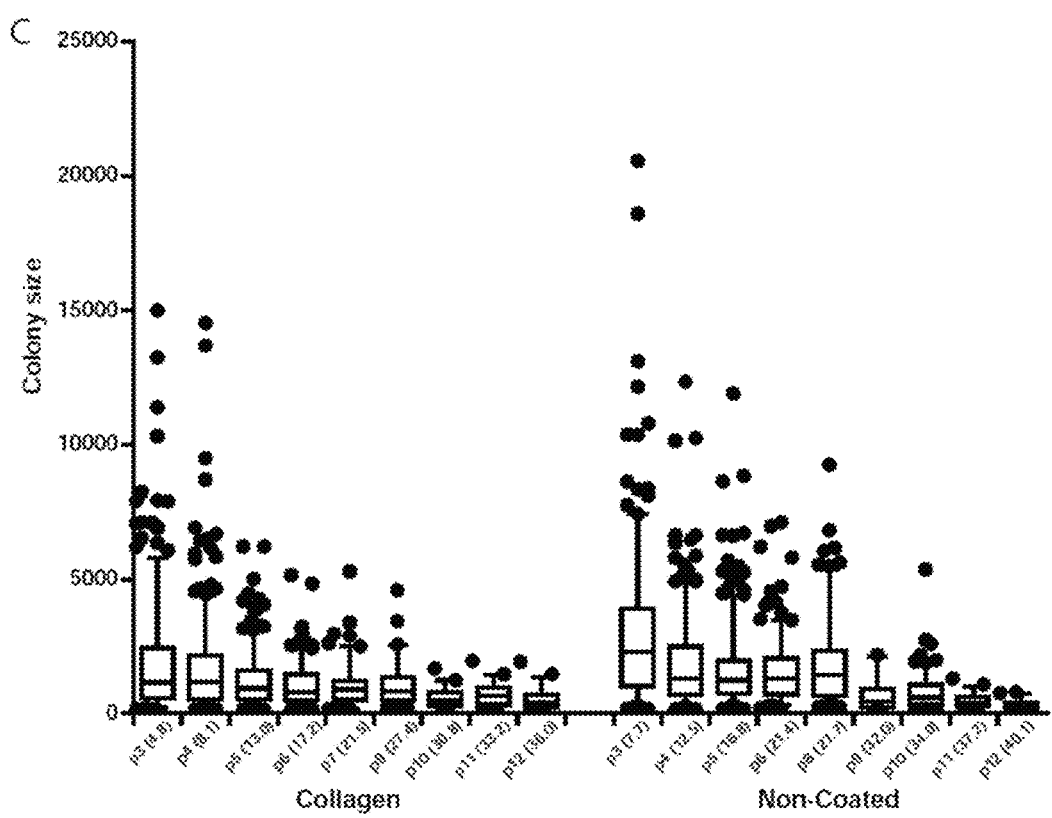

It was found that keratinocytes can be cultured on either collagen 1 or non-coated plastic plates. In long-term culture of cells grown in KCM4 on either collagen 1 coated or non-coated plates, there was no difference in the growth rate of keratinocytes on either surface (FIG. 10A). However, primary keratinocytes grown on the non-coated plates performed slightly better in the CFA than those grown on collagen (FIGS. 10B-C). For example, at 21.5 doublings (P6 for NC and P7 for C1) cells cultured on C1 produced average of 40.3 colonies/per well and an average colony size of 1033 units while cells cultured on NC averaged 80.7 colonies/per well and 1564 units.

Figure 11:
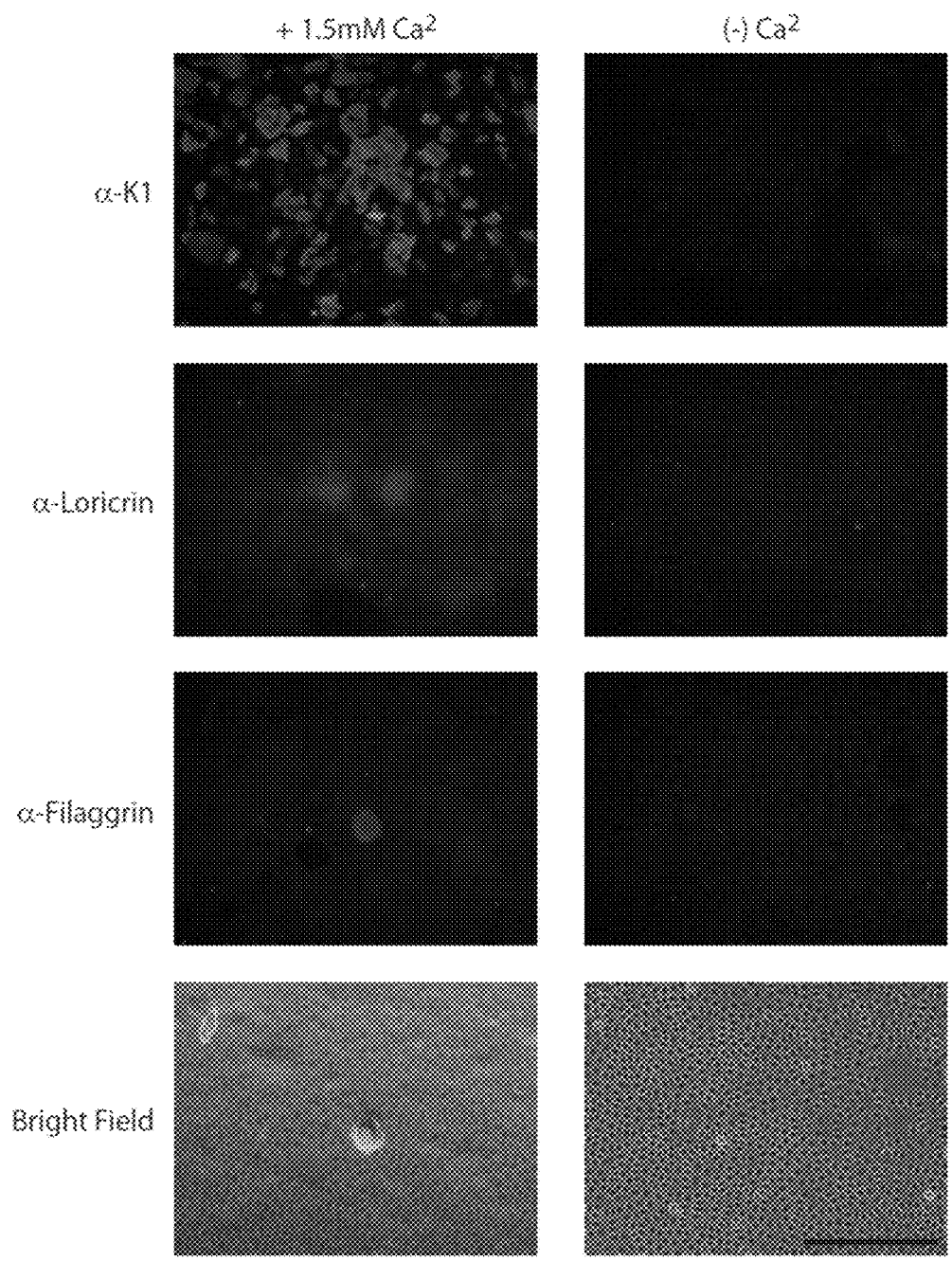
FIG. 11. Keratinocytes cultured in KCM4 express differentiation markers in response to high calcium. Passage 3 keratinocytes were treated with 1.5 mM $Ca^{2+}$ for three days and assessed by immunocytochemistry for expression of differentiation markers Keratin 1, Loricrin and Filaggrin. Scale bar 200 µm.

Keratinocytes cultured in KCM4 were found to express differentiation markers in response to high calcium. Passage 3 keratinocytes were treated with 1.5 mM $Ca^{2+}$ for 3 days and assessed by immunocytochemistry for expression of differentiation markers Keratin 1, Loricrin, and Filaggrin. Expression of all three differentiation markers was detected in the high $Ca^{2+}$ treated wells and absent in the untreated wells (FIG. 11).

Figure 12A:
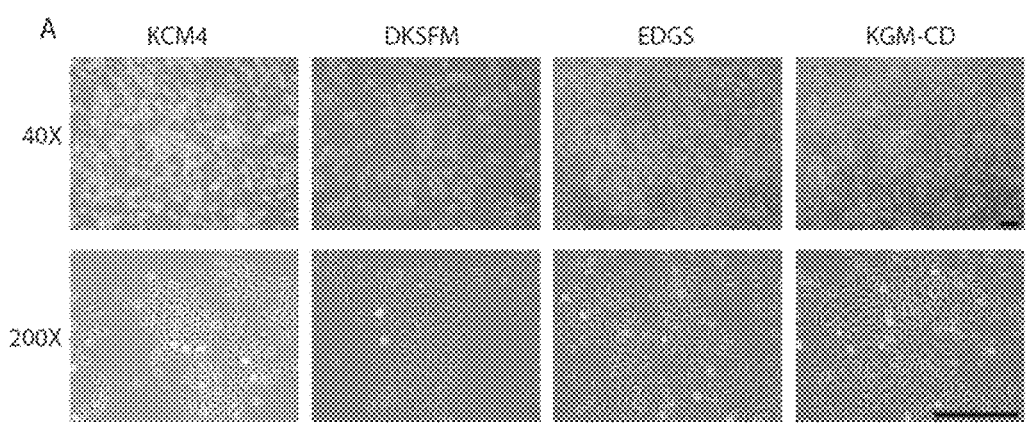
Figure 12D:
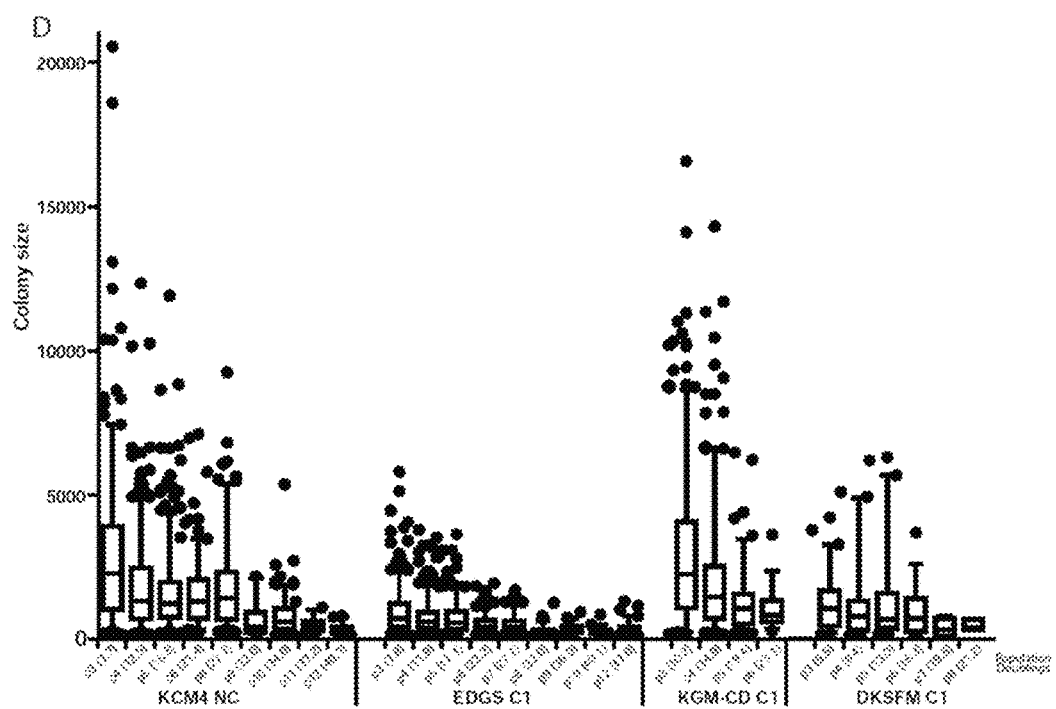

KCM4 was determined to perform similarly to commercially available chemically defined media. KCM4 was compared to three different chemically defined media: Invitrogen's Defined Keratinocyte Serum Free Medium (DKSFM), EpiLife Defined Growth Supplement (EDGS), and Lonza's Keratinocyte Growth Medium-Chemically Defined (KGM-CD). Cells cultured in the commercial media were grown on collagen coated plates, as recommended by the manufacturer. Cells grown in the different media exhibited different morphologies. KCM4 and DKSFM cultured cells both grew in colonies while EDGS and KGM-CD cultured cells were more motile and covered the plate more uniformly as they grew (FIG. 12A). KCM4 and KGM-CD cultured cells were generally smaller than DKSFM or EDGS cells. In long-term culture of primary keratinocytes in different media (FIG. 12B), cells cultured in KGM-CD grew the fastest, but senesced after only 26 population doublings. Cells cultured in EDGS grew at a slightly reduced rate and achieved 50+ population doublings. KCM4 and DKSFM cultured cells grew at the same reduced rate in the early passages. DKSFM cells senesced after 21 doublings while KCM4 cells grew for 40+ population doublings. CFAs of keratinocytes cultured in different media were performed (FIGS. 12C-D). Cells cultured in KCM4 performed slightly better in the CFAs than cells cultured in the commercial media. Keratinocytes cultured in DKSFM and KGM-CD produced fewer colonies and lost colony forming ability much earlier compared to those cultured in KCM4 and EDGS. Keratinocytes cultured in KCM4 were able to produce more colonies in later passages and larger colonies compared to those cultured in EDGS.

Methods

Isolation of Primary Keratinocytes from Newborn Foreskin.

Figure 7D:
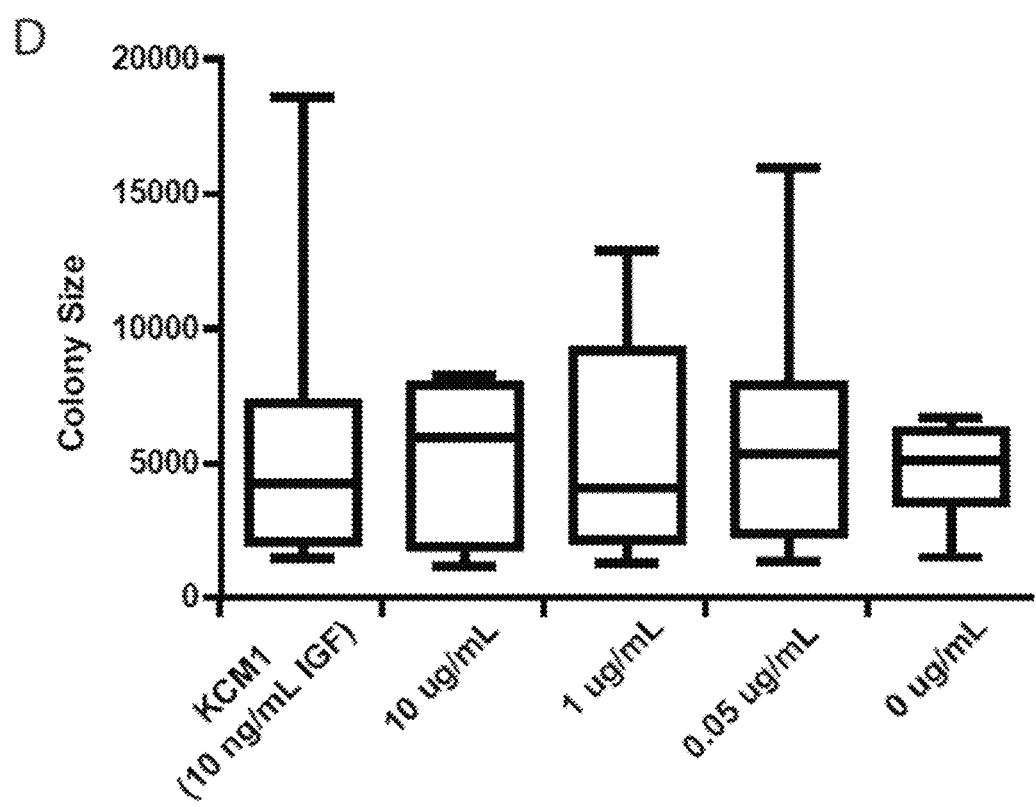

Foreskins were purchased from the Cooperative Human Tissue Network at Vanderbilt University Medical Center. The subcutaneous fat was removed from each tissue. The foreskin was incubated epidermis side down in 3 mL of 5 mg/mL dispase in TeSR basal medium for approximately 16 hours at 4° C. The epidermis was peeled away from the dermis and incubated with 2 mL 0.05% trypsin at 37° C. for 5 minutes. The cell suspension was rigorously pipetted to loosen cells from the intact epidermal pieces and subsequently passed through an 80 µm cell filter. The trypsin was neutralized with 0.5 mg/mL of trypsin inhibitor. The cells were centrifuged at 1200 rpm for 4 min. Cells were plated in keratinocyte culture media as follows. For FIGS. 7 and 8, newly isolated keratinocytes were plated and cultured through P1 in KCM1 with 10 µg/mL insulin. Cells were frozen at the end of P1. Upon thawing, cells were expanded for one passage in KCM1 (10 µg/mL insulin), then the media was changed to the indicated formulations. For FIGS. 9, 10, and 12, keratinocytes were plated in the same medium used for culturing, with the exception of KCM4+VEGF. For this condition, VEGF was added at the beginning of P3. For FIG. 11, newly isolated keratinocytes were plated and cultured through P1 in KCM1 with 10 µg/mL insulin and BMP4. Cells were frozen at the end of P1. Upon thawing, the media was changed to KCM4.

Culture of Primary Keratinocytes.

Keratinocytes were maintained in the indicated medium and passaged every 4-5 days (at ~80% confluence). For passage, keratinocytes were incubated with a 0.1% Trypsin in Versene solution at 37° C. for 5 minutes. The trypsin was neutralized with 0.5 mg/mL of trypsin inhibitor. The cells were centrifuged at 1200 rpm for 4 min. Cells were counted with a Cellometer (Nexcelom). Cells (25,000-50,000) were plated per well of 6-well plates in the indicated keratinocyte culture media. Media was changed every other day.

Differentiation of Primary Keratinocytes.

Keratinocytes were cultured in KCM4 and at 80%-90% confluence, cells were either treated with 1.5 mM $Ca^{2+}$ for 3 days or fixed (no calcium control). Cells were assessed by immunocytochemistry for expression of differentiation markers K1, Loricrin, and Filaggrin using polyclonal rabbit antibodies (Covance).

Morphology Analysis.

Cells were assessed visually for overall health of the culture and for typical keratinocyte morphology and growth pattern.

Population Doubling.

Cells were maintained by serial passage at ~80% confluence until senescence. The total number of cell doublings for each passage was calculated using the following formula: 3.32 log(N/No). Where No refers to the number of cells plated at the beginning of each passage and N is the number of cells recovered at the end of each passage.

Colony Formation Assays (CFA).

Cells were plated at low density (250 cells/well of a 6-well plate) and allowed to grow for 8-12 days. For FIGS. 7 and 8, cells were switched from the indicated culture medium to KCM1 (10 µg/mL insulin) at the beginning of the CFA. Keratinocytes were cultured in KCM1 (10 µg/mL insulin) for 12 days and colony size was measured. For FIGS. 9, 10, and 12, the CFAs were performed with the medium used for maintaining the keratinocytes. KCM4 needed to be supplemented with 5 µg/mL insulin to support colony growth. Colonies were allowed to grow for 8 days and colony size was measured.

Following culture, plates were fixed and stained with Hoechst stain. The whole plate was imaged at 40× with an ImageXpress high content imager (Molecular Devices). The total number of colonies per well was counted and the size of each colony was measured using ImageJ software. Colony counts are shown in bar graphs where bar height represents the average number of colonies/well for each passage and the error bars represent the standard deviation. Colony sizes are presented in box and whisker plots where the center line represents the median, the box represents the inter-quartile range and the whiskers represent the 5-95 percentile. Data that fall outside this range are plotted individually.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,030,015
U.S. Pat. No. 5,145,770
U.S. Pat. No. 5,298,417
U.S. Pat. No. 5,843,780
U.S. Pat. No. 6,548,297
U.S. Pat. No. 6,833,269
U.S. Pat. Publication 2003/0211603
U.S. Pat. Publication 2007/0116680
U.S. Pat. Publication 2007/0238170
U.S. Pat. Publication 2008/0171385
PCT Publn. WO 97/37009
PCT Publn. WO 98/30679
PCT Publn. WO 01/88100
PCT Publn. WO 2005/080554
PCT Publn. WO 2005/123902
PCT Publn. WO 2009/149233
PCT Publn. WO 2010/141801
A practical approach, 1987.
Amit et al., Dev. Bio., 227:271-278, 2000.
Andrews et al., In: Teratocarcinomas and Embryonic Stem Cells, Robertson (Ed.), IRL Press, 207-246, 1987.
Animal Cell Culture, 1987.
Bolivar-Flores et al., Burns, 16:3-8, 1990.
Boyer et al., Cell, 122(6):947-956, 2005.
Chambers et al., Cell, 113(5):643-655, 2003.
Chen et al., Nature Methods, 8:424-429, 2011.
Culture of Animal Cells: a manual of basic techniques (3.sup.rd edition), R. I. Freshney (ed.), Wiley-Liss, Inc., 1994.
Current Protocols in Molecular Biology and Short Protocols in Molecular Biology, 1987; 1995. Embryonic Stem Cell Differentiation in vitro, 1993.
Evans et al., Theriogenology, 33:125-129, 1990.
Evans and Kaufman, Nature, 292:154-156, 1981.
Fernandes et al., Nature Cell Biology, 6:1082-1093, 2004.
Gallico et al., New Eng. J. Med., 311:448-451, 1984.
Gene Targeting, A Practical Approach, 1993.
Gene Transfer Vectors for Mammalian Cells, Miller, J and Calos, M P (eds.), Cold Spring Harbor Laboratory Press, New York, N.Y., 1987.
Guide to Techniques in Mouse Development, Abelson, J N; Simon, M I; DePamphili, M L (eds.), Methods in Enzymology, 1993.
Heighten et al., J. Am. Acad. Dermatol., 14:399-405, 1986.
Hochereau-de Reviers and Perreau, Reprod. Nutr. Dev., 33:475-493, 1993.
Hogan et al., Manipulating the Mouse Embryo, A Laboratory Manual, Genes and Development, 9:1559-1678, 1994.
In vitro Methods in Pharmaceutical Research, J. V. Castell and M. J. Gomez-Lechon (eds.), Academic Press, 1997.
Jainchill et al., J. Virol., 4(5):549-53, 1969.
Kawasaki et al., Induction of midbrain dopaminergic neurons from ES cells by stromal cell-derived inducing activity, Neuron, 28:31-40, 2000.
Keller et al., Curr. Opin. Cell Biol., 7(6):862-9, 1995.
Klimanskaya et al., Lancet., 365(9471):1636-41, 2005.
Kodama et al., J. Cell Physiol., 112(1):89-95, 1982.
Kuzuya et al., Arterioscl. Thromb. Vascular Biol., 21:765, 2001.
Lian et al., A Small Molecule Inhibitor of Src Family Kinases Promotes Simple Epithelial Differentiation of Human Pluripotent Stem Cells, PLoS ONE, 8:e60016, 2013.
Ludwig et al., Nat. Biotechnol., 24(2):185-187, 2006b.
Ludwig et al., Nat. Methods, 3(8):637-46, 2006a.
Martin, Proc. Natl. Acad. Sci. USA, 78(12):7634-8, 1981.
Metallo et al., Human Embryonic Stem Cell-Derived Keratinocytes Exhibit an Epidermal Transcription Program and Undergo Epithelial Morphogenesis in Engineered Tissue Constructs, Tissue Eng. Part A, 16:213-223, 2010.
Moore and Piedrahita, In Vitro Cell Biol. Anim., 33:62-71, 1997.
Moore and Piedrahita, Mol. Reprod. Dev., 45:139-144, 1996.
Nakano et al., In Vitro Development of Primitive and Definitive Erythrocytes from Different Precursors, Science, 272:722-724, 1996.
Phillips et al., J. Am. Acad. Derm., 21:191, 1989.
Piedrahita et al., Theriogenology, 34:879-901, 1990.
Piedrahita et al., Biol. Reprod., 58:1321-1329, 1998.
Rathjen et al., Properties and uses of Embryonic Stem Cells: Prospects for Application to Human Biology and Gene Therapy, Reprod. Fertil. Dev., 10:31-47, 1998.
Reubinoff et al., Nat. Biotechnol., 18:399-404, 2000.

Rheinwald and Green, *Cell*, 6:331-343, 1975.
Smith, In: *Origins and Properties of Mouse Embryonic Stem Cells, Annu. Rev. Cell. Dev. Biol.*, 2000.
Strojek et al., *Theriogenology*, 33:901-903, 1990.
Takahashi et al., *J. Biol. Chem.*, 278:18664-18670, 2003.
Takahashi et al., *Cell*, 126:663-676, 2006.
Takahashi et al., *Cell*, 131:861-872, 2007.
Takahashi and Yamanaka, *Cell*, 126:663-676, 2006.
Thomson et al., *Proc. Natl. Acad. Sci. U.S.A.*, 92:7844-7848, 1995.
Thomson et al., *Science*, 282:1145, 1998.
Thomson and Marshall, *Curr. Top. Dev. Biol.*, 38:133-165, 1998.
Thomson and Odorico, *J. Trends. Biotechnol.*, 18:53-57, 2000.
Watanabe et al., *Nat. Neurosci.*, 8(3):288-296, 2005.
Wheeler, *Reprod. Pert. Dev.*, 6:563-568, 1994.
Wianny et al., *Biol. Reprod.*, 57:756-764, 1997.
Xu et al., *Nat. Biotechnol.*, 19:971-974, 2001.
Yang and Anderson, *Theriogenology*, 38:315-335, 1992.
Ying et al., *Cell*, 115:281-292, 2003.
Yu et al., *Science*, 318:1917-1920, 2007.
Yu et al., *Science*, 324:797-801, 2009.
Yu and Thompson, *Genes Dev.*, 22(15):1987-1997, 2008.

What is claimed is:

1. A method for providing engraftable human keratinocyte stem cells by differentiation of human pluripotent stem cells comprising:
    (a) forming aggregates of the pluripotent stem cells in a suspension culture in the presence of a defined basal medium;
    (b) culturing the aggregates in a suspension culture in the presence of an initiation culture medium comprising retinoic acid and bone morphogenetic protein 4 (BMP4) to effect the formation of initiated aggregates;
    (c) culturing the initiated aggregates in a keratinocyte progenitor culture medium comprising cholera toxin and a transforming growth factor beta receptor 1 (TGFBR1) kinase inhibitor to effect the formation of a cell population comprising keratinocyte progenitors; and
    (d) culturing the keratinocyte progenitors in a keratinocyte stem cell maturation medium comprising cholera toxin and vascular endothelial growth factor (VEGF) to effect the formation of a cell population comprising engraftable keratinocyte stem cells,
wherein the keratinocyte stem cells express cytokeratin 15 and CD49f.

2. The method of claim 1, further comprising maintaining the keratinocyte stem cells in culture in a keratinocyte stem cell maintenance medium comprising cholera toxin and a TGFBR1 kinase inhibitor.

3. The method of claim 2, wherein the keratinocyte stem cells are maintained for at least five population doublings.

4. The method of claim 3, wherein the keratinocyte stem cells are maintained for at least ten population doublings.

5. The method of claim 1, wherein the keratinocyte stem cells are at least 90% pure.

6. The method of claim 1, wherein the keratinocyte stem cells are at least 95% pure.

7. The method of claim 1, wherein the pluripotent stem cells are induced pluripotent stem (iPS) cells.

8. The method of claim 1, wherein the pluripotent stem cells are cultured in a serum-free medium prior to step (a).

9. The method of claim 1, wherein the pluripotent stem cells are cultured on a non-cellular matrix component prior to step (a).

10. The method of claim 1, wherein the culture medium in step (a) is a chemically-defined culture medium.

11. The method of claim 1, wherein the culturing in step (a) is performed for a time period of about one day.

12. The method of claim 1, wherein the culturing in step (a) is further performed in the presence of a myosin light chain kinase inhibitor.

13. The method of claim 1, wherein the culturing in step (b) is performed for a time period from about one day to about five days.

14. The method of claim 13, wherein the culturing in step (b) is performed for a time period of about three days.

15. The method of claim 1, wherein the suspension culture in step (a) and/or (b) is maintained as a static suspension culture.

16. The method of claim 1, wherein the suspension culture in step (a) and/or (b) is maintained as a dynamic suspension culture.

17. The method of claim 1, wherein the culturing in step (c) is performed for a time period from about eight to about 14 days.

18. The method of claim 17, wherein the culturing in step (c) is performed for a time period of about ten days.

19. The method of claim 1, wherein the keratinocyte progenitor culture medium further comprises epidermal growth factor (EGF), fibroblast growth factor 1 (FGF1), a cyclic AMP analog, niacinamide, ascorbic acid, or a combination thereof.

20. The method of claim 19, wherein the keratinocyte progenitor culture medium further comprises EGF and niacinamide.

21. The method of claim 1, wherein the culturing in step (c) is performed as an adherent culture.

22. The method of claim 1, wherein the culturing in step (c) is performed on an extracellular matrix component.

23. The method of claim 1, wherein the culturing in step (c) is performed on a non-cellular matrix component.

24. The method of claim 1, wherein the keratinocyte progenitors formed in step (c) express cytokeratin 14 and/or p63.

25. The method of claim 1, wherein a calcium level in the keratinocyte progenitor culture medium is not greater than about 0.2 mM.

26. The method of claim 1, wherein the culturing in step (d) is performed for a time period from about four days to about eight days.

27. The method of claim 1, wherein the culturing in step (d) is performed for a time period of about six days.

28. The method of claim 1, wherein the keratinocyte stem cell maturation medium further comprises EGF, FGF1, a cyclic AMP analog, niacinamide, or a combination thereof.

29. The method of claim 1, wherein the culturing in step (d) is performed as an adherent culture.

30. The method of claim 1, wherein the culturing in step (d) is performed on an extracellular matrix component.

31. The method of claim 1, wherein the culturing in step (d) is performed on a non-cellular matrix component.

* * * * *

UNITED STATES PATENT AND TRADEMARK OFFICE
CERTIFICATE OF CORRECTION

PATENT NO. : 10,047,341 B2
APPLICATION NO. : 14/881747
DATED : August 14, 2018
INVENTOR(S) : Junying Yu et al.

Page 1 of 1

It is certified that error appears in the above-identified patent and that said Letters Patent is hereby corrected as shown below:

In the Claims

In Claim 1, Column 37, Line 40, delete "TGFBR1" and insert --TGFβR1-- therefor.

In Claim 2, Column 37, Line 53, delete "TGFBR1" and insert --TGFβR1-- therefor.

Signed and Sealed this
Fourth Day of December, 2018

Andrei Iancu
*Director of the United States Patent and Trademark Office*